United States Patent
Matsushita

(10) Patent No.: US 9,389,412 B2
(45) Date of Patent: Jul. 12, 2016

(54) VARIABLE-WAVELENGTH INTERFERENCE FILTER, OPTICAL FILTER DEVICE, OPTICAL MODULE AND ELECTRONIC APPARATUS

(71) Applicant: Seiko Epson Corporation, Tokyo (JP)

(72) Inventor: Tomonori Matsushita, Chino (JP)

(73) Assignee: Seiko Epson Corporation (JP)

( * ) Notice: Subject to any disclaimer, the term of this patent is extended or adjusted under 35 U.S.C. 154(b) by 188 days.

(21) Appl. No.: 13/888,615

(22) Filed: May 7, 2013

(65) Prior Publication Data

US 2013/0306838 A1 Nov. 21, 2013

(30) Foreign Application Priority Data

May 18, 2012 (JP) ................. 2012-114154

(51) Int. Cl.
*G02B 26/00* (2006.01)
*G01J 1/44* (2006.01)
*G01J 3/26* (2006.01)
*G01J 3/28* (2006.01)
*G01J 3/02* (2006.01)
G01N 21/65 (2006.01)
G01J 3/12 (2006.01)

(52) U.S. Cl.
CPC ............... *G02B 26/001* (2013.01); *G01J 1/44* (2013.01); *G01J 3/027* (2013.01); *G01J 3/26* (2013.01); *G01J 3/2823* (2013.01); *G01J 2003/1247* (2013.01); *G01N 21/658* (2013.01)

(58) Field of Classification Search
CPC .... B81B 2201/033; G01J 3/32; G01J 3/0227; G01J 3/0229; G01J 2003/1226; G01J 2003/1234; G01J 2003/1239; G01J 2003/1247; G01J 2003/1252; G01J 3/26; G01J 1/44; G01J 3/2823; G01J 3/027; G02B 26/0841; G02B 26/0833; G02B 26/0866; G02B 26/085; G02B 26/0816; G02B 26/0858; G02B 26/001; G02B 26/02; G02B 5/28; G01N 21/658

USPC ................. 250/226; 359/221.2, 223.1, 224.1, 359/224.2, 850, 290

See application file for complete search history.

(56) References Cited

U.S. PATENT DOCUMENTS

| | | | |
|---|---|---|---|
| 4,859,060 A | 8/1989 | Katagiri et al. | |
| 5,906,429 A | 5/1999 | Mori et al. | |
| 6,015,610 A * | 1/2000 | Minor et al. | ............... 428/315.7 |

(Continued)

FOREIGN PATENT DOCUMENTS

| | | | |
|---|---|---|---|
| JP | S62-257032 A | 11/1987 | |
| JP | 07-065412 A | 3/1995 | |

(Continued)

*Primary Examiner* — Francis M Legasse, Jr.
(74) *Attorney, Agent, or Firm* — Harness, Dickey & Pierce, P.L.C.

(57) ABSTRACT

A variable-wavelength interference filter includes: a first substrate; a second substrate facing the first substrate; a first reflection layer provided on a surface facing the second substrate, of the first substrate; a second reflection layer which is provided on a surface facing the first substrate, of the second substrate, and faces the first reflection layer via an inter-layer gap; and an electrostatic actuator which flexes the second substrate in a direction toward the first substrate and thus changes the inter-layer gap. The first reflection layer and the second reflection layer have a reflectance characteristic showing a higher reflectance to light with a second wavelength that is shorter than a first wavelength, than a reflectance to light with the first wavelength.

12 Claims, 11 Drawing Sheets

(56) References Cited

U.S. PATENT DOCUMENTS

| | | | |
|---|---|---|---|
| 7,310,153 B2* | 12/2007 | Kiesel et al. | 356/519 |
| 7,734,131 B2* | 6/2010 | Lin et al. | 385/27 |
| 2009/0246576 A1 | 10/2009 | Terazaki et al. | |
| 2012/0109584 A1* | 5/2012 | Urushidani | 702/189 |
| 2012/0200926 A1* | 8/2012 | Matsushita | G01J 3/26 359/578 |

FOREIGN PATENT DOCUMENTS

| | | |
|---|---|---|
| JP | 07-074077 A | 3/1995 |
| JP | 07-243963 | 9/1995 |
| JP | 2009-238603 A | 10/2009 |
| JP | 2009-251105 A | 10/2009 |
| JP | 2010-266876 A | 11/2010 |

* cited by examiner

VARIABLE-WAVELENGTH INTERFERENCE FILTER, OPTICAL FILTER DEVICE, OPTICAL MODULE AND ELECTRONIC APPARATUS

BACKGROUND

1. Technical Field

The present invention relates to a variable-wavelength interference filter, an optical filter device, an optical module, and an electronic apparatus.

2. Related Art

According to the related art, a variable-wavelength interference filter is known in which a pair of reflection layers facing each other is provided and the distance between the reflection layers is changed to extract light with a predetermined wavelength from measuring target light (see, for example, JP-A-7-243963).

The variable-wavelength interference filter (optical cavity) described in JP-A-7-243963 includes a first substrate and a second substrate facing each other, high reflection layers arranged on the respective substrates and facing each other via an inter-layer gap, and electrodes arranged on the respective substrates and facing each other. In such a variable-wavelength interference filter, by applying a voltage between the electrodes and thus deforming the second substrate and adjusting the inter-layer gap, the wavelength of light extracted by the variable-wavelength interference filter can be changed.

Meanwhile, in the variable-wavelength interference filter described in JP-A-7-243963, by applying a voltage between the electrodes, the second substrate is flexed and driven in a direction which narrows the inter-layer gap. Therefore, when the inter-layer gap is narrowed in order to extract light on the short-wavelength side, there is a problem that the half-value width of light transmitted through the variable-wavelength interference filter increases (resolution decreases) as the inter-layer gap is narrowed because of the flexure and gradient of the second substrate.

SUMMARY

An advantage of some aspects of the invention is that a variable-wavelength interference filter, an optical filter device, an optical module and an electronic apparatus which are capable of properly extracting light in a preset wavelength range.

The invention can be implemented as the following forms or application examples.

Application Example 1

A variable-wavelength interference filter according to this application example includes: a first substrate; a second substrate facing the first substrate; a first reflection layer provided on a surface facing the second substrate, of the first substrate; a second reflection layer which is provided on a surface facing the first substrate, of the second substrate, and faces the first reflection layer via an inter-layer gap; and a gap changing portion which flexes the second substrate in a direction toward the first substrate and thus changes the inter-layer gap between the first reflection layer and the second reflection layer. The first reflection layer and the second reflection layer have a reflectance characteristic showing a higher reflectance to light with a second wavelength that is shorter than a first wavelength, than a reflectance to light with the first wavelength.

In this application example, the gap changing portion is an electrostatic actuator made up of a first electrode provided on the first substrate and a second electrode provided on the second substrate. In such an electrostatic actuator, the electrodes can be arranged facing each other, thus enabling simplification of the configuration and reduction in the size and thickness of the variable-wavelength interference filter. Also, the inter-layer gap can be easily changed simply by changing a voltage applied between the electrodes, and therefore gap control of the inter-layer gap can be carried out easily.

When the gap changing portion flexes the second substrate in a direction which narrows the inter-layer gap, the flexure of the second substrate causes a slight flexure of the second reflection layer as well. Therefore, in such a variable-wavelength interference filter, since the flexure of the second reflection layer increases as the inter-layer gap decreases, the half-value width of the optical characteristic (transmission characteristic of a transmission peak wavelength) of the variable-wavelength interference filter increases toward shorter wavelengths.

In this case, if reflection layers having a reflection characteristic showing a reflectance that falls toward the short-wavelength side are used as the first reflection layer and the second reflection layer, the half-value width increases further toward the short-wavelength side because of a combined effect of the influence of the flexure of the second reflection layer with the influence of the reflection characteristic of the reflection layers, and the resolution on the short-wavelength side falls significantly. Also, even if reflection layers having a reflection characteristic showing a constant reflectance to each wavelength are used as the first reflection layer and the second reflection layer, the resolution on the short-wavelength side falls because of the reduction in the resolution caused by the flexure of the second reflection layer.

On the other hand, in this application example, reflection layers having a reflection characteristic showing a reflectance that rises toward the short-wavelength side are used as the first reflection layer and the second reflection layer. In this case, the influence of the flexure of the second reflection layer and the influence of the reflection characteristic of the reflection layers offset each other. Thus, even when the inter-layer gap is changed, the half-value width of the transmission peak wavelength is substantially uniform. Therefore, the resolution of the variable-wavelength interference filter can be substantially uniform irrespective of the wavelength of light to be extracted.

Application Example 2

In the variable-wavelength interference filter according to the above application example, it is preferable that the first reflection layer and the second reflection layer are made of AlAs.

In this application example, AlAs is used for the first reflection layer and the second reflection layer. AlAs as an optical film has a reflectance that rises toward the short-wavelength side and a reflection characteristic over a broad range including visible rays. Therefore, the variable-wavelength interference filter can extract light with a desired wavelength with uniform resolution over a broad wavelength range.

Application Example 3

In the variable-wavelength interference filter according to the above application example, it is preferable that the first wavelength is 700 nm and the shorter wavelength is 400 nm.

In this application example, the first reflection layer and the second reflection layer has a reflectance characteristic showing a reflectance that rises toward the short-wavelength side in a visible range. Therefore, the variable-wavelength interference filter can extract light with a desired wavelength with uniform resolution over a broad wavelength range including visible rays.

Application Example 4

In the variable-wavelength interference filter according to the above application example, it is preferable that the first wavelength is 2500 nm and the shorter wavelength is 700 nm.

In this application example, the first reflection layer and the second reflection layer has a reflectance characteristic showing a reflectance that rises toward the short-wavelength side in a near-infrared range. Therefore, the variable-wavelength interference filter can extract light with a desired wavelength with uniform resolution over a broad wavelength range including near-infrared rays.

Application Example 5

In the variable-wavelength interference filter according to the above application example, it is preferable that the second substrate includes a movable portion provided with the second reflection layer, and a holding portion provided on an outer peripheral part of the movable portion and having a smaller rigidity than the movable portion, and that the rigidity of the holding portion is asymmetrical about a center of movement of the movable portion.

In this application example, the second substrate is configured in such a way that the movable portion provided with the second reflection layer is held by the holding portion. In this case, since the rigidity of the holding portion is smaller than the movable portion, when stress to flex the second substrate is applied by the gap changing portion, the holding portion flexes and thus displacing the movable portion. In such a configuration, by configuring the holding portion to flex easily when stress is applied by the gap changing portion, the stress to flex the second substrate can be decreased. For example, with the gap changing portion which generates stress to flex the second substrate as a voltage is applied, the voltage to flex the second substrate by a predetermined amount can be reduced and power saving can be realized.

Meanwhile, in such a configuration, since the movable portion is displaced by the flexure of the holding portion, there is little deformation in the shape of the movable portion in relation to the holding portion. In this case, it can be considered that the influence on the optical characteristic, of the flexure of the second reflection layer when the inter-layer gap is varied, is reduced and therefore the resolution on the short-wavelength side falls below the resolution on the long-wavelength side because of the influence of the reflection characteristic of the reflection layer.

On the other hand, in this application example, the rigidity of the holding portion is asymmetrical about the center of movement of the movable portion. In this case, when the inter-layer gap is increased by the gap changing portion, the difference in the rigidity of the holding portion causes the inter-layer gap to vary in the state where the movable portion is sloped. Therefore, the gradient angle of the second reflection layer changes in relation to the first reflection layer according to the inter-layer gap, and the gradient angle increases toward the short-wavelength side. Thus, the resolution on the short-wavelength side falls (the half-value width increases) because of the influence of the gradient of the second reflection layer. In this case, the influence of the flexure of the second reflection layer and the influence of the gradient of the second reflection layer on one hand, and the influence of the reflection characteristic of the reflection layer on the other, offset each other. Even when the inter-layer gap is changed, the half-value width of the transmission peak wavelength is substantially uniform. Therefore, in this application example, substantially uniform resolution can be realized irrespective of the wavelength of light extracted by the variable-wavelength interference filter.

Application Example 6

In the variable-wavelength interference filter according to the above application example, it is preferable that the second substrate includes a movable portion provided with the second reflection layer, and a holding portion provided on an outer peripheral part of the movable portion and having a smaller rigidity than the movable portion, and that the gap changing portion is arranged at a position that is asymmetrical about a center of movement of the movable portion in a plan view in which the first substrate and the second substrate are viewed from a direction of substrate thickness.

In this application example, since the movable portion and the holding portion are provided on the second substrate, as in the above application example, the stress to flex the second substrate by the gap changing portion can be reduced.

Also, in this application example, the position where the stress to flex the second substrate is applied by the gap changing portion is asymmetrical about the center of movement of the movable portion. Therefore, also in this case, when the inter-layer gap is increased by the gap changing portion, the inter-layer gap varies in the state where the movable portion (second reflection layer) is sloped, according to the position where the stress is applied. Therefore, the influence of the flexure of the second reflection layer and the influence of the gradient of the second reflection layer on one hand, and the influence of the reflection characteristic of the reflection layer on the other, offset each other. Even when the inter-layer gap is changed, the half-value width of the transmission peak wavelength is substantially uniform. Thus, also in this application example, substantially uniform resolution can be realized irrespective of the wavelength of light extracted by the variable-wavelength interference filter.

Application Example 7

In the variable-wavelength interference filter according to the above application example, it is preferable that the second substrate includes a bonding portion bonded to the first substrate, and a flexing portion which flexes in a direction of approaching from the first substrate with stress applied by the gap changing portion, and that the second reflection layer is provided on the flexing portion.

In this application example, the second reflection layer is provided on the flexing portion provided on the second substrate. In such a configuration, when the inter-layer gap is narrowed by the gap changing portion, the flexing portion flexes, causing the second reflection layer to flex. Therefore, the influence of the flexure of the second reflection layer and the influence of the reflection characteristic of the reflection layers offset each other. Even when the inter-layer gap is changed, the half-value width of the transmission peak wavelength is substantially uniform. Thus, substantially uniform resolution can be realized irrespective of the wavelength of light extracted by the variable-wavelength interference filter.

Application Example 8

In the variable-wavelength interference filter according to the above application example, it is preferable that the flexing portion has an equal thickness dimension.

In this application example, since the flexing portion is formed to a uniform thickness dimension, manufacturability of the second substrate can be improved. Also, the thickness dimension of the bonding portion and the thickness dimension of the flexing portion can be made the same. In this case, processing such as etching on the second substrate is not necessary. Therefore, manufacturability can be improved further and the manufacturing cost can be reduced further. For example, a thin sheet glass with a thickness of 30 to 100 μm may be used as the second substrate.

Application Example 9

An optical filter device according to this application example includes: a first substrate; a second substrate facing the first substrate; a first reflection layer provided on a surface facing the second substrate, of the first substrate; a second reflection layer which is provided on a surface facing the first substrate, of the second substrate, and faces the first reflection layer via an inter-layer gap; a gap changing portion which flexes the second substrate in a direction toward the first substrate and thus changes the inter-layer gap between the first reflection layer and the second reflection layer; and a casing accommodating the first substrate and the second substrate. The first reflection layer and the second reflection layer have a reflectance characteristic showing a higher reflectance to light with a second wavelength that is shorter than a first wavelength, than a reflectance to light with the first wavelength.

In this application example, a variable-wavelength interference filter is accommodated in the casing. Since the variable-wavelength interference filter is protected by the casing, damage to the variable-wavelength interference filter due to external factors can be prevented.

Application Example 10

An optical module according to this application example includes: a first substrate; a second substrate facing the first substrate; a first reflection layer provided on a surface facing the second substrate, of the first substrate; a second reflection layer which is provided on a surface facing the first substrate, of the second substrate, and faces the first reflection layer via an inter-layer gap; a gap changing portion which flexes the second substrate in a direction toward the first substrate and thus changes the inter-layer gap between the first reflection layer and the second reflection layer; and a light receiving portion where light transmitted through the first reflection layer or the second reflection layer is received. The first reflection layer and the second reflection layer have a reflectance characteristic showing a higher reflectance to light with a second wavelength that is shorter than a first wavelength, than a reflectance to light with the first wavelength.

In this application example, the light receiving portion where light transmitted through a variable-wavelength interference filter and the first reflection layer or the second reflection layer is received is provided.

As in the above application examples, the variable-wavelength interference filter can properly extract light with a desired wavelength from a preset wavelength range. Therefore, in the optical module, too, there is no inconvenience such as the inability to extract light with a required wavelength and the light extracted by the variable-wavelength interference filter can be securely received by the light receiving portion.

Application Example 11

An electronic apparatus according to this application example includes: a first substrate; a second substrate facing the first substrate; a first reflection layer provided on a surface facing the second substrate, of the first substrate; a second reflection layer which is provided on a surface facing the first substrate, of the second substrate, and faces the first reflection layer via an inter-layer gap; a gap changing portion which flexes the second substrate in a direction toward the first substrate and thus changes the inter-layer gap between the first reflection layer and the second reflection layer; a light receiving portion where light transmitted through the first reflection layer or the second reflection layer is received; and an analysis processing portion where, based on the light received by the light receiving portion, a characteristic of the light is analyzed. The first reflection layer and the second reflection layer have a reflectance characteristic showing a higher reflectance to light with a second wavelength that is shorter than a first wavelength, than a reflectance to light with the first wavelength.

In this application example, as in the above application examples, the variable-wavelength interference filter can properly extract light with a desired wavelength from a preset wavelength range. Therefore, in the electronic apparatus, too, there is no inconvenience such as the inability to extract light with a required wavelength and various kinds of processing can be carried out accurately based on the light extracted by the variable-wavelength interference filter.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment of the invention will be described with reference to the drawings.

Configuration of Spectroscopic Measuring Device

Figure 1:
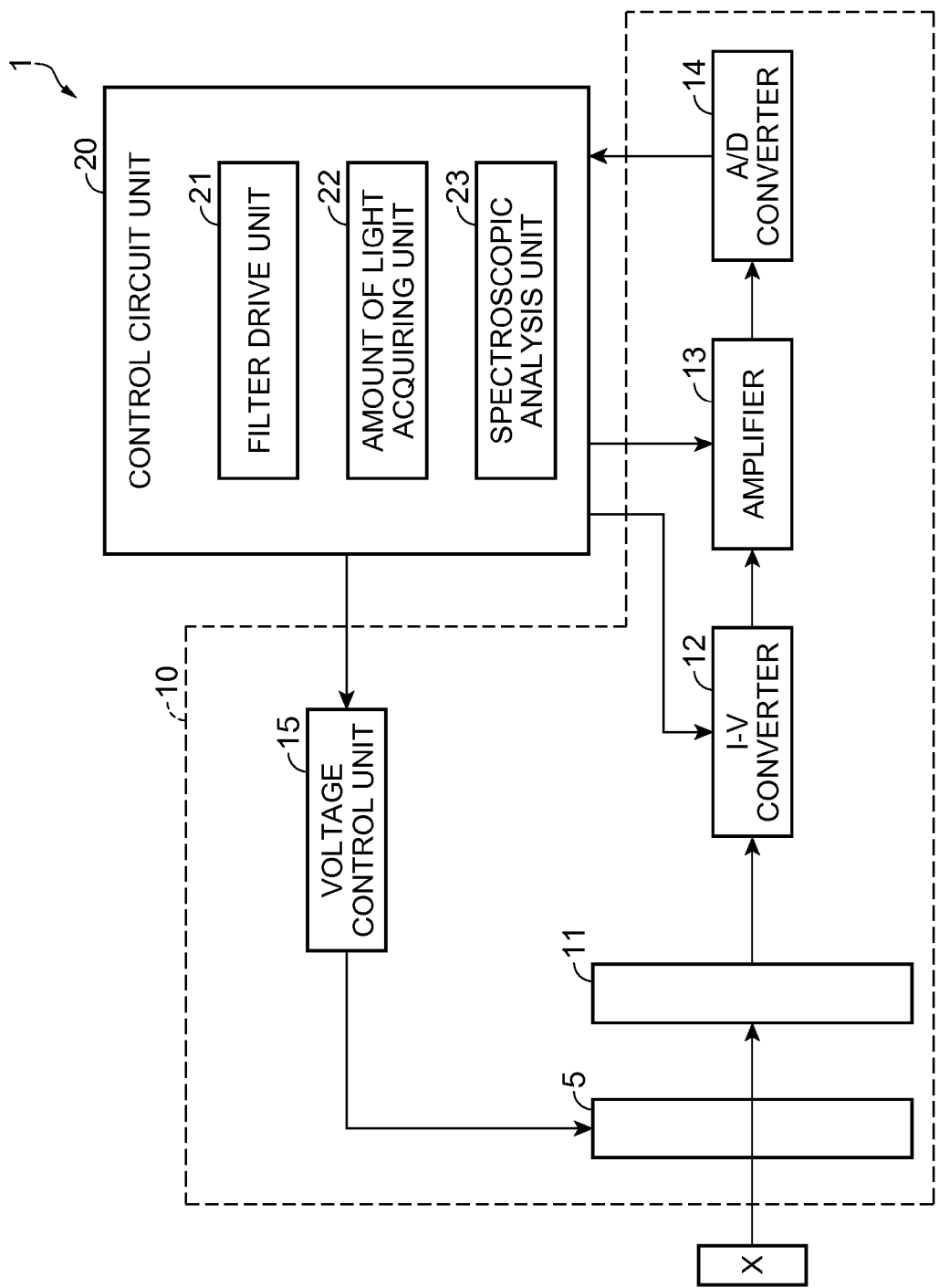
FIG. 1 is a block diagram showing the schematic configuration of a spectroscopic measuring device according to a first embodiment.

FIG. 1 is a block diagram showing the schematic configuration of a spectroscopic measuring device according to the embodiment.

A spectroscopic measuring device 1 is a device which analyzes light intensity of each wavelength of measuring target light reflected by, for example, a measuring target X, and measures the spectrum thereof. While an example in which measuring target light reflected by the measuring target X is measured is illustrated in this embodiment, if a light emitting body, for example, a liquid crystal panel or the like, is used as the measuring target X, light emitted from the light emitting body may be used as measuring target light.

This spectroscopic measuring device 1 has an optical module 10 and a control circuit unit 20 which processes a signal outputted from the optical module 10.

Configuration of Optical Module

The optical module 10 includes a variable-wavelength interference filter 5, a detection unit 11, an I-V converter 12, an amplifier 13, and A/D converter 14, and a voltage control unit 15.

In this optical module 10, measuring target light reflected by the measuring target X is guided to the variable-wavelength interference filter 5 through an incidence system (not shown) and the light transmitted through the variable-wavelength interference filter 5 is received by the detection unit 11. A detection signal output from the detection unit 11 is outputted to the control circuit unit 20 via the I-V converter 12, the amplifier 13 and the A/D converter 14.

Configuration of Variable-Wavelength Interference Filter

Next, the variable-wavelength interference filter 5 incorporated in the optical module 10 will be described.

Figure 2:
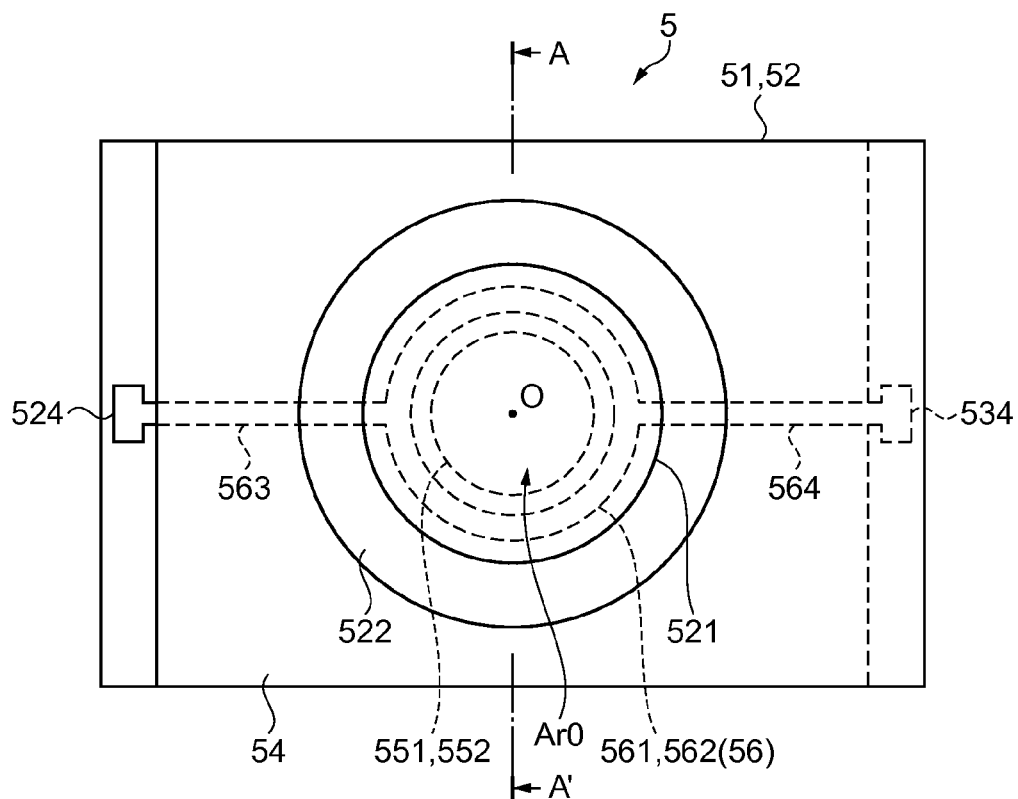
FIG. 2 is a plan view showing the schematic configuration of a variable-wavelength interference filter according to the first embodiment.
Figure 3:
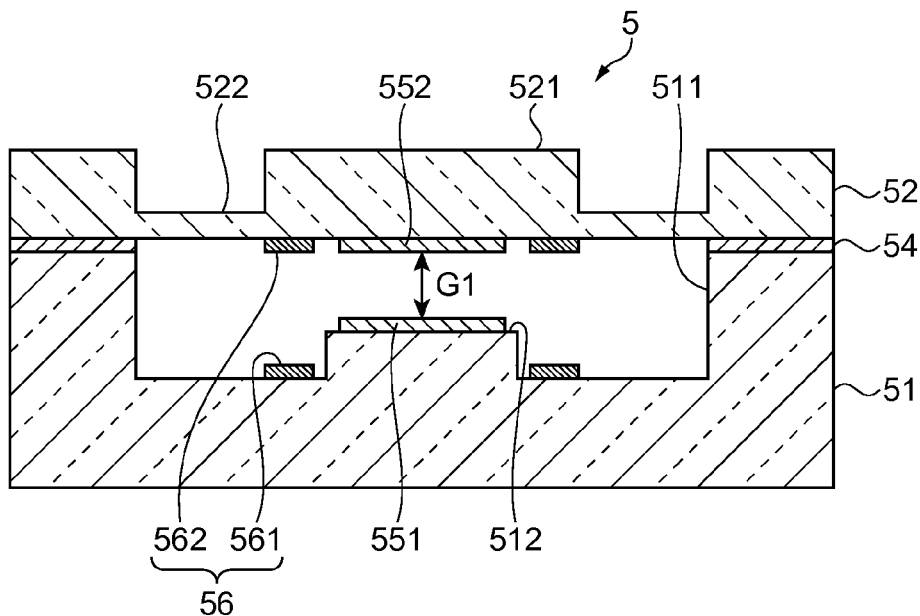
FIG. 3 is a cross-sectional view of the variable-wavelength interference filter, taken along A-A' in FIG. 2.

FIG. 2 is a plan view showing the schematic configuration of the variable-wavelength interference filter. FIG. 3 is a cross-sectional view of the variable-wavelength interference filter, taken along A-A' in FIG. 2.

As shown in FIG. 2, the variable-wavelength interference filter 5 includes a first substrate 51 and a second substrate 52.

Each of these substrates 51, 52 is made of, for example, various kinds of glass such as soda-lime glass, crystalline glass, quartz glass, lead glass, potassium glass, borosilicate glass, and non-alkaline glass, or a crystal or the like. The first substrate 51 and the second substrate 52 are bonded together with a bonding film 54. As the bonding film 54, for example, a plasma polymer film containing siloxane as a principal component or the like can be used.

A first reflection layer 551 is provided on a surface of the first substrate 51 facing the second substrate 52. A second reflection layer 552 is provided on a surface of the second substrate 52 facing the first substrate 51. The first reflection layer 551 and the second reflection layer 552 are arranged facing each other via an inter-layer gap G1.

Also, an electrostatic actuator 56 constituting the gap changing portion according to the invention is provided. This electrostatic actuator 56 includes a first electrode 561 provided on the surface of the first substrate 51 facing the second substrate 52, and a second electrode 562 provided on the surface of the second substrate 52 facing the first substrate 51.

The variable-wavelength interference filter 5 has a light interference area (effective area Ar0) where the first reflection layer 551 and the second reflection layer 552 overlap each other, in a plan view as viewed from the direction of the thickness of the substrates 51, 52 (hereinafter, referred to as a filter plan view, in some cases), and light transmitted through this effective area Ar0 becomes incident on the detection unit 11.

Configuration of First Substrate

Next, the configuration of the first substrate 51 will be described in detail.

Figure 4:
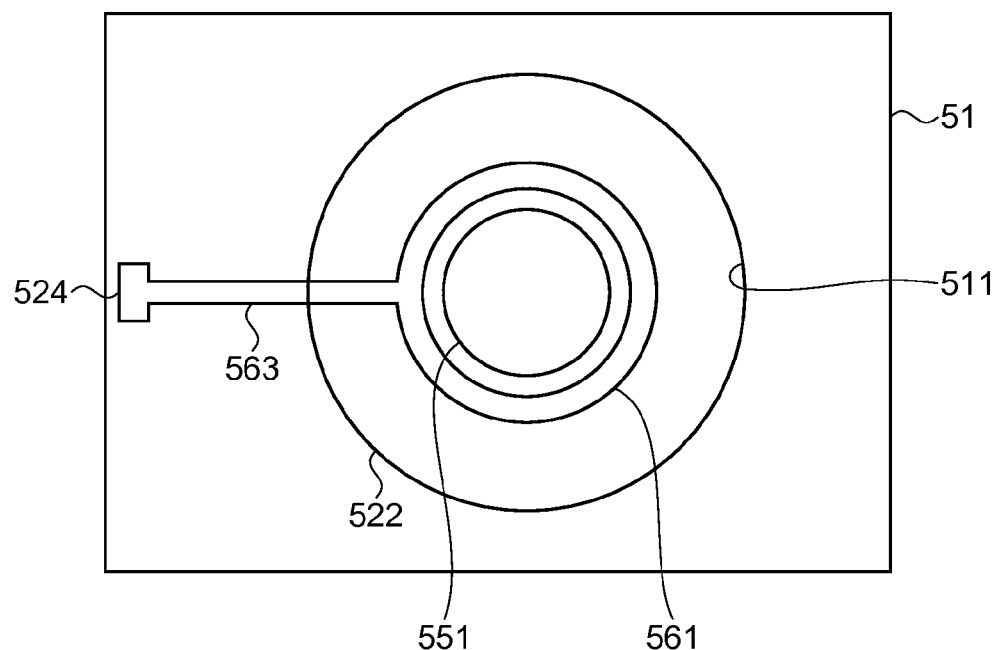
FIG. 4 is a plan view of a first substrate as viewed from the side of a second substrate according to the first embodiment.

FIG. 4 is a plan view of the first substrate as viewed from the second substrate side. The first substrate 51 is formed by etching a base material with a thickness of, for example, 500 μm. On the first substrate 51, a circular recessed portion 511 centering around the center of the first substrate 51 is provided by etching. Moreover, at a central part of the recessed portion 511, a columnar protruding portion 512 protruding from the bottom surface of the recessed portion 511 is formed.

On a flat surface of the protruding portion 512, the first reflection layer 551 having a light reflection characteristic and a light transmission characteristic is formed. The first reflection layer 551 is formed at a central part of the protruding portion 512, and the ring-shaped first electrode 561 is formed surrounding the first reflection layer 551.

The first reflection layer 551 is made of AlAs or the like and has a characteristic showing a higher reflectance toward the short-wavelength side.

The first electrode 561 is connected to a first lead-out electrode 563. The first lead-out electrode 563 is led out to one of the four sides of the first substrate 51. The first lead-out electrode 563 is connected to a first terminal extracting portion 524 formed on a side portion of the first substrate 51.

The first electrode 561, the first lead-out electrode 563 and the first terminal extracting portion 524 are electrically conductive films, using an ITO film, for example. These electrically conductive films may also use a Cr/Au film formed by stacking an Au film on an underlying Cr film.

Configuration of Second Substrate

Figure 5:
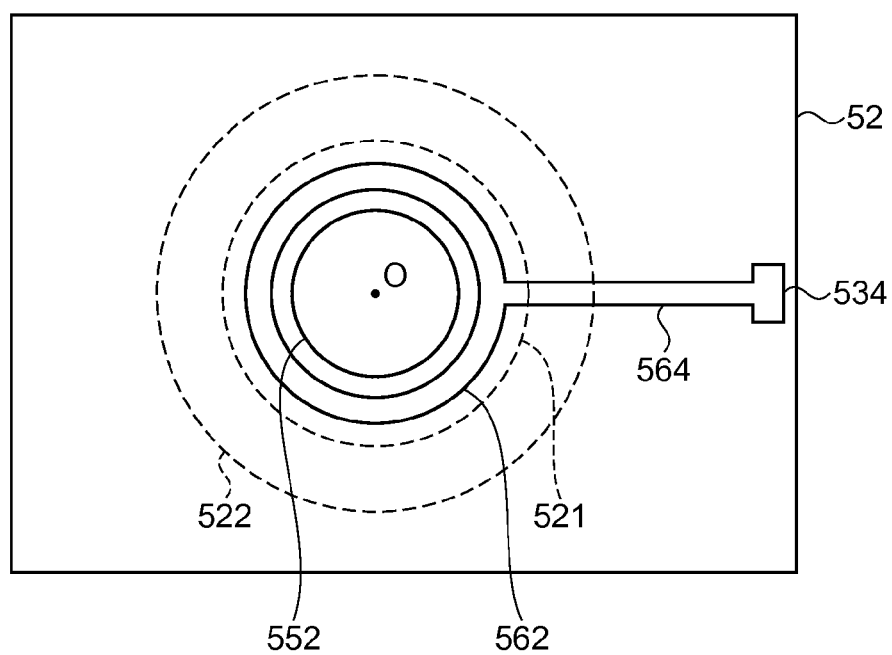
FIG. 5 is a plan view of the second substrate as viewed from the side of the first substrate according to the first embodiment.

Next, the configuration of the second substrate 52 will be described in detail. FIG. 5 is a plan view of the second substrate as viewed from the first substrate side.

As shown in FIGS. 2, 3 and 5, the second substrate 52 has a circular movable portion 521 centering around a filter center point O, and a holding portion 522 coaxial with the movable portion 521 and holding the movable portion 521.

One end side of the second substrate 52 forms a second terminal extracting portion 534.

The movable portion 521 is formed with a greater thickness dimension than the holding portion 522. For example, in this embodiment, the movable portion 521 is formed with the same thickness dimension as the second substrate 52.

The second reflection layer 552 is provided on a surface of the movable portion 521 facing the first substrate 51. As the second reflection layer 552, a reflection layer with the same configuration as the first reflection layer 551 is used.

Also, the second electrode 562 constituting the electrostatic actuator 56 is provided on the surface of the movable portion 521 facing the first substrate 51. The second electrode 562 is provided on the outer peripheral side of the effective area Ar0 and is formed in a ring shape centering around the filter center point O, as viewed in a filter plan view.

A second lead-out electrode 564 is connected to an outer peripheral edge of the second electrode 562. This second lead-out electrode 564 extends from the second electrode 562 toward the second terminal extracting portion 534. A distal end portion of the second lead-out electrode 564 is exposed outside and is connected to the voltage control unit 15, for example, via an FPC (flexible printed circuit) or lead wire.

For the second electrode 562 and the second lead-out electrode 564, any electrode material that can form an electrically conductive electrode may be used. For example, ITO, a Cr/Au multilayer electrode or the like can be used. Also, an insulating film to secure withstand voltage may be stacked on the second electrode 562.

The holding portion 522 is a diaphragm surrounding the movable portion 521 and has a smaller rigidity in the direction of thickness than the movable portion 521.

Therefore, the holding portion 522 can flex more easily than the movable portion 521 and can be flexed toward the first substrate 51 by a very small electrostatic attraction. In this case, since the movable portion 521 has a greater thickness dimension and rigidity than the holding portion 522, the flexure of the movable portion 521 can be restrained even when an electrostatic attraction causes a flexing force to act on the second substrate 52. Thus, the flexure of the second reflection layer 552 formed on the movable portion 521 is restrained as well.

While the diaphragm-like holding portion 522 is illustrated as an example in this embodiment, the holding portion is not limited to this example and, for example, beam-like holding portions arranged at an equal angular distance around the filter center point O may also be provided.

On the surface of the second substrate 52 facing the first substrate 51, as described above, a bonding portion is provided across a substrate outer peripheral part on the outer peripheral side of the holding portion 522, and the first substrate 51 and the second substrate 52 are bonded together with the bonding film 54.

Configuration of Detection Unit, I-V Converter, Amplifier, A/D Converter and Voltage Control Unit Next, back to FIG. 1, the detection unit 11 of the optical module 10 will be described.

The detection unit 11 receives light transmitted through the effective area Ar0 of the variable-wavelength interference filter 5 and outputs a detection signal based on the amount of light received.

The I-V converter 12 converts the detection signal inputted from the detection unit 11 to a voltage value and outputs the voltage value to the amplifier 13.

The amplifier 13 amplifies the voltage corresponding to the detection signal (detection voltage) inputted from the I-V converter 12.

The A/D converter 14 converts the detection voltage (analog signal) input from the amplifier 13 to a digital signal and outputs the digital signal to the control circuit unit 20.

The voltage control unit 15 applies a voltage to the electrostatic actuator 56 of the variable-wavelength interference filter 5 under the control of the control circuit unit 20. Thus, an electrostatic attraction is generated between the first electrode 561 and the second electrode 562 of the electrostatic actuator 56. The movable portion 521 is displaced in a direction toward the first substrate 51, and the amount of gap of the inter-layer gap G1 is set to a predetermined value.

Configuration of Control Circuit Unit

Next, the control circuit unit 20 of the spectroscopic measuring device 1 will be described.

The control circuit unit 20 is formed, for example, by a combination of a CPU, a memory and the like, and controls the operation of the entire spectroscopic measuring device 1. This control circuit unit 20 includes a filter drive unit 21, an amount of light acquiring unit 22, and a spectroscopic analysis unit 23, as shown in FIG. 1.

The control circuit unit 20 has a storage unit (not shown) which stores various data. V-λ data for controlling the electrostatic actuator 56 is stored in this storage unit. In the V-λ data, a peak wavelength of light transmitted through the effective area Ar0 in relation to a voltage applied to the electrostatic actuator 56 is recorded.

The filter drive unit 21 sets the voltage applied to the electrostatic actuator 56 of the variable-wavelength interference filter 5, referring to the V-λ data stored in the storage unit, and outputs a control signal to the voltage control unit 15.

Thus, the voltage control unit 15 applies the preset voltage to the first electrode 561 and the second electrode 562, thus changing the inter-layer gap G1.

The amount of light acquiring unit 22 acquires the amount of light detected by the detection unit 11 and stores the amount of light in the storage unit.

The spectroscopic analysis unit 23 analyzes the spectrum of measuring target light, based on the amount of light with respect to each wavelength, acquired by the amount of light acquiring unit 22 and stored in the storage unit.

Optical Characteristics of Variable-Wavelength Interference Filter

Next, optical characteristics of the variable-wavelength interference filter 5 in the spectroscopic measuring device 1 will be described with reference to the drawings.

Figure 6:
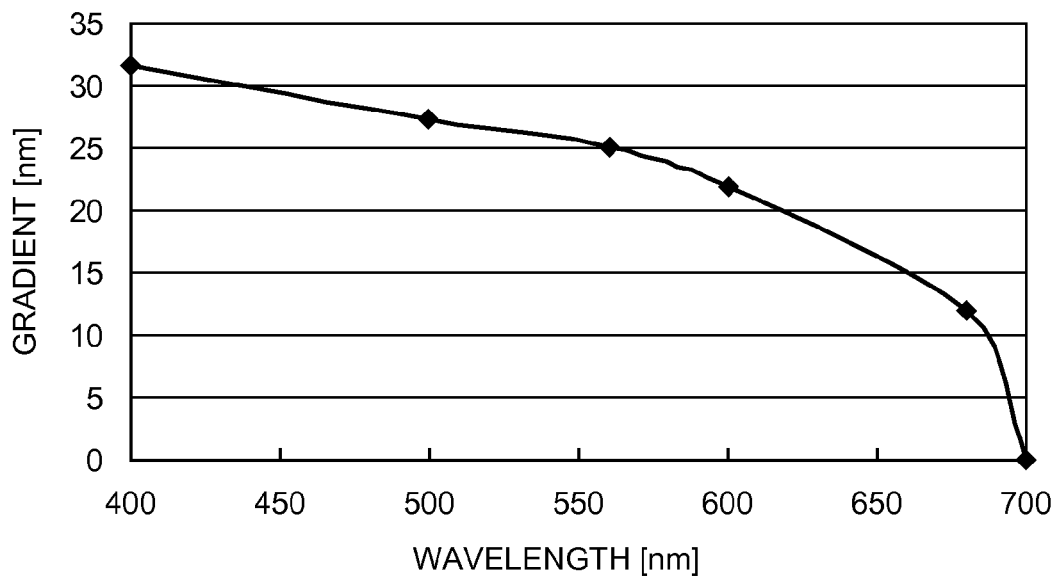
FIG. 6 shows the gradient of a second reflection layer in the case where the inter-layer gap is changed in the variable-wavelength interference filter of the embodiment.
Figure 7:
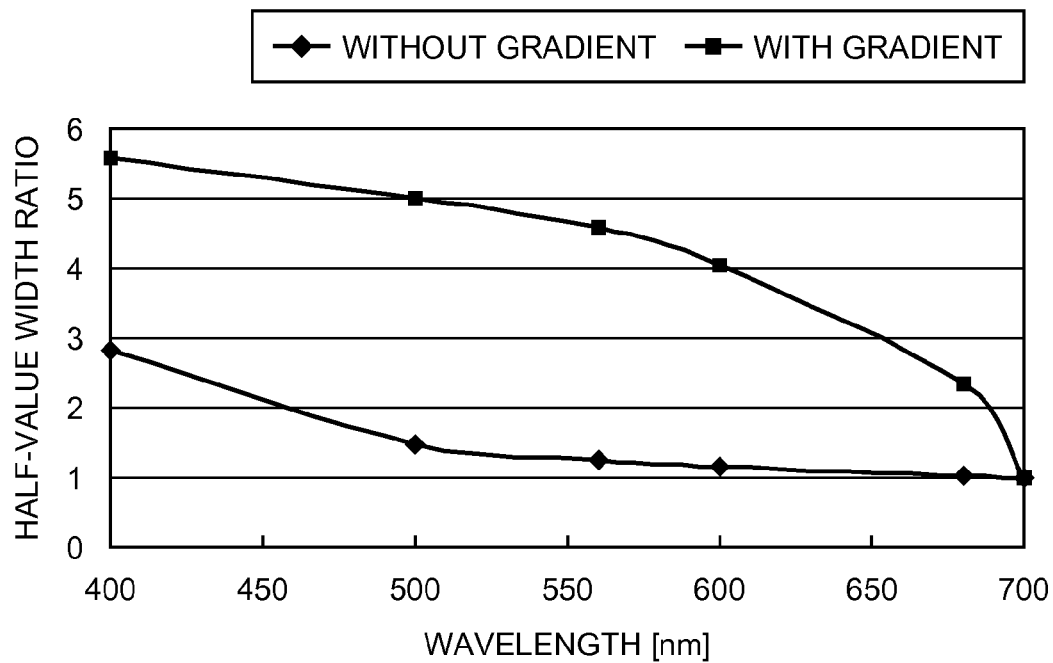
FIG. 7 shows the half-value width ratio of a transmitted transmission peak wavelength in the case where an Ag alloy is used for the reflection layers in the variable-wavelength interference filter.
Figure 8A:
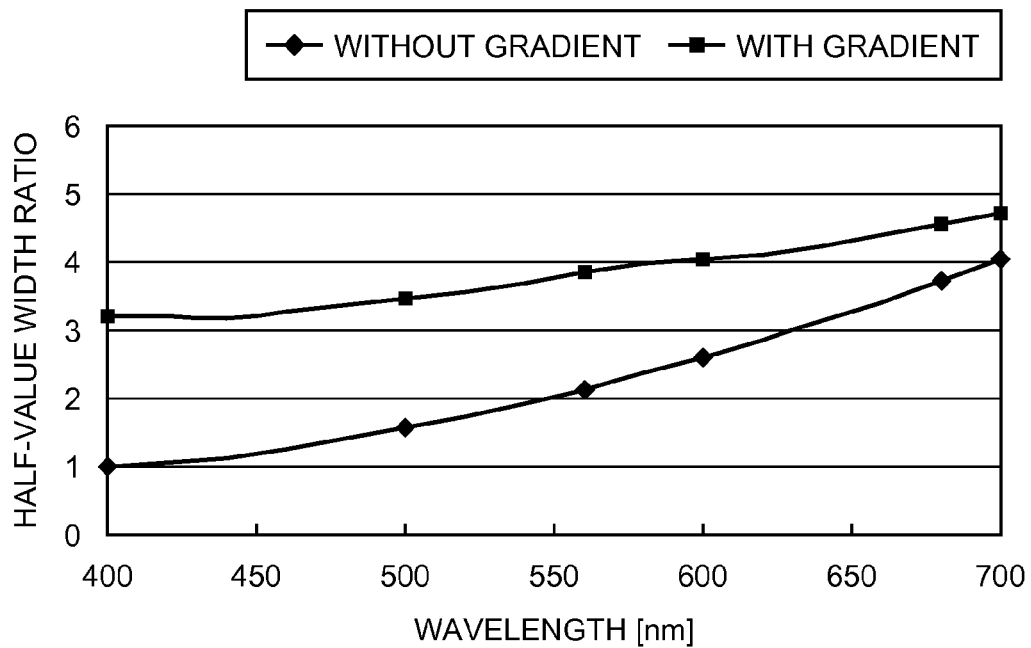
FIGS. 8A and 8B show the half-value width ratio of a transmitted transmission peak wavelength in the case where AlAs and Al are used for the reflection layers in the variable-wavelength interference filter.
Figure 8B:
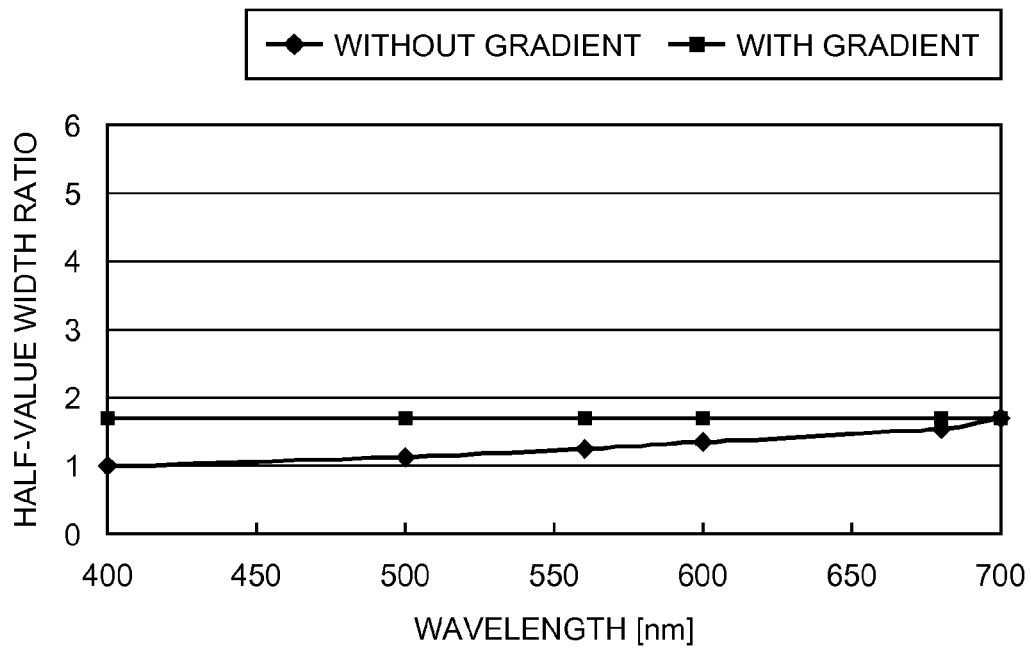

FIG. 6 shows an example of gradient of the second reflection layer in the case where the inter-layer gap G1 is changed in the variable-wavelength interference filter of this embodiment. FIG. 7 shows the half-value width ratio of a transmitted transmission peak wavelength in the case where an Ag alloy is used for the reflection layers in the variable-wavelength interference filter. FIGS. 8A and 8B show the half-value width ratio of a transmitted transmission peak wavelength in the case where AlAs and Al are used for the reflection layers in the variable-wavelength interference filter.

As shown in FIG. 6, the gradient of the second reflection layer 552 increases as the inter-layer gap G1 decreases (as the wavelength becomes shorter).

Here, in the variable-wavelength interference filter which extracts specific light through multiple interference by the pair of reflection layers, the reflection characteristic changes according to the reflectance of the reflection layers. Therefore, when reflection layers having a reflectance that rises from the short-wavelength side toward the long-wavelength side, such as Ag or Ag alloy, are used as the first reflection layer 551 and the second reflection layer 552, the half-value width of the transmission peak wavelength decreases from the short-wavelength side toward the long-wavelength side.

FIG. 7 shows the half-value width ratio of the transmission peak wavelength with and without a gradient of the reflection layer (Ag alloy) in the variable-wavelength interference filter. This FIG. 7 shows changes in the half-value width ratio, based on the half-value width in the case where the reflection layer has no gradient at a transmission wavelength of 700 nm.

In the case where the reflection layer has no gradient, in the configuration using an Ag alloy for the reflection layer, the reflectance of the reflection layer is large on the long-wavelength side and the gradient of the second reflection layer 552 is small. Therefore, as shown in FIG. 7, light with a transmission peak wavelength having a small half-value width and high accuracy can be obtained. However, on the short-wavelength side, the reflectance of the reflection layer is small and the half-value width is approximately twice as large as on the long-wavelength side.

In practice, since the gradient of the second reflection layer 552 increases, the half-value width of the transmission peak wavelength increases further. The half-value width is approximately 4.5 times larger on the short-wavelength side than on the long-wavelength side. Therefore, the resolution of the variable-wavelength interference filter falls and the half-value width varies depending on the measuring target wavelength, thus causing a problem that light with the transmission peak wavelength cannot be extracted with uniform resolution.

FIG. 8A shows the half-value width ratio of the transmission peak wavelength with and without a gradient of the reflection layer in the case where AlAs is used for the reflection layer of this embodiment. This FIG. 8A shows changes in the half-value width ratio based on the half-value width in the case where the reflection layer has no gradient at a transmission wavelength of 400 nm.

In the case where AlAs is used for the reflection layer and the reflection layer has no gradient, the reflectance is small on the long-wavelength side and the half-value width is approximately three times larger than on the short-wavelength side. As can be seen, it shows the opposite tendency to the case where an Ag alloy is used for the reflection layer.

In practice, since the second reflection layer 552 has a gradient, this gradient offsets the change in the half-value width. The half-value width on the long-wavelength side is approximately 1.7 times larger than on the short-wavelength. Thus, the change in the half-value width can be restrained.

Therefore, whatever wavelength is extracted from a measuring target wavelength range, light with a substantially uniform half-value width can be extracted, as shown in FIG. 8A. Thus, there is no variation in the resolution depending on the extracted wavelength of light. In such a configuration, since light of each wavelength can be extracted under the same conditions, highly accurate spectroscopic measurement can be implemented by the spectroscopic measuring device 1.

Next, a case where Al is used for the reflection layer will be described.

FIG. 8B shows the half-value width ratio of the transmission peak wavelength with and without a gradient of the reflection layer in the case where Al is used for the reflection layer of this embodiment. This FIG. 8B shows changes in the half-value width ratio based on the half-value width in the case where the reflection layer has no gradient at a transmission wavelength of 400 nm.

In the case where Al is used for the reflection layer and the reflection layer has no gradient, the reflectance on the long-wavelength side is greater than on the short-wavelength side. This is a similar tendency to the case where AlAs is used for the reflection layer, but the amount of change is smaller.

In practice, since the second reflection layer 552 has a gradient, this gradient offsets the change in the half-value width. A substantially uniform half-value width can be obtained in the entire transmission range.

By the way, if the Al reflection layer and the AlAs reflection layer are compared, the Al reflection has a lower light transmittance than the AlAs reflection layer in a near-infrared range. As the wavelength becomes longer, the extinction coefficient of Al becomes larger and therefore the transmittance falls. Therefore, when the Al reflection layer is used for the near-infrared range, it is difficult to secure a necessary amount of light. Meanwhile, the AlAs reflection layer has a high transmittance even in the near-infrared range and an amount of light can be secured easily.

Thus, reflection layers needs to be selected in consideration of the wavelength range to be used.

Advantageous Effects of First Embodiment

In this embodiment, the first reflection layer 551 and the second reflection layer 552 have a reflectance characteristic showing a reflectance that increases from the short-wavelength side toward the long-wavelength side. Thus, the half-value width of light extracted by the variable-wavelength interference filter 5 can be made uniform.

That is, in the configuration in which the reflection layer of an Ag alloy as shown in FIG. 8A is used and the inter-layer gap 01 is narrowed, when light on the long-wavelength side is transmitted through the variable-wavelength interference filter, the second reflection layer 552 has no flexure or gradient and the reflectance of the reflection layer is high. Therefore, high-resolution light with a small half-value width can be extracted. Meanwhile, in such a related-art variable-wavelength interference filter, when light on the short-wavelength side is transmitted, the second reflection layer 552 has flexure or gradient and the reflectance of the reflection layer is lower than on the long-wavelength side. Therefore, low-resolution light with a large half-value width is extracted. Thus, with the related-art variable-wavelength interference filter, the half-value width decreases from the short-wavelength side toward the long-wavelength side and it is difficult to extract light with uniform resolution.

On the contrary, according to this embodiment, on the short-wavelength side, even if the reflectance of the reflection layers 551, 552 is lower than on the long-wavelength side, the flexure or gradient of the second reflection layer 552 is restrained and therefore light with higher resolution can be extracted, compared with the related-art variable-wavelength interference filter. Meanwhile, on the long-wavelength side, the resolution is lower than in the related-art variable-wavelength interference filter, because of the influence of the flexure or gradient of the second reflection layer 552. Therefore, in this embodiment, whatever wavelength of light is extracted from a preset wavelength range, the half-value width can be made substantially uniform and the light can be extracted with substantially constant resolution.

Thus, in the spectroscopic measuring device 1, for example, when acquiring a spectrum of measuring target light, the inconvenience that measuring reliability on the short-wavelength side is lower than measuring reliability on the long-wavelength side, or the like, can be avoided and an accurate spectrum can be acquired.

Also, according to this embodiment, AlAs films are used as the first reflection layer 551 and the second reflection layer 552. Such AlAs film has a reflection characteristic over a broad wavelength range from visible range to near-infrared range. Therefore, the a broad range can be set as a measuring target wavelength range of the variable-wavelength interference filter 5.

Second Embodiment

Next, a second embodiment of the invention will be described.

In the first embodiment, the electrostatic actuator 56 includes the ring-shaped first electrode 561 and second electrode 562 centering around the filter center point O. Therefore, since the electrostatic actuator 56 causes an electrostatic attraction to act on the movable portion 521 in a well-balanced manner with respect to the filter center point O, the gradient of the movable portion 521 (second reflection layer 552) may be small in some cases even when the inter-layer gap G1 is changed. Also, with the configuration in which the movable portion 521 is held by the holding portion 522, the holding portion 522 with a low rigidity has a large amount of flexure and the amount of flexure of the movable portion 521 is restrained to a small amount.

In such a case, the influence of the reflectance characteristics of the reflection layers 551, 552 on the optical characteristics of the variable-wavelength interference filter 5 is stronger than the influence of the slight gradient or slight flexure of the movable portion 521 on the optical characteristics of the variable-wavelength interference filter 5. Therefore, though the half-value width of the transmission peak wavelength can be decreased on the long-wavelength side, the half-value width of the transmission peak wavelength on the long-wavelength side does not increase and optical characteristics with a uniform half-value width may not be obtained. Even in this case, the difference in the half-value width of the transmission peak wavelength between respective wavelengths can be reduced, compared with the related-art configuration. However, in the second embodiment, a configuration which enables further reduction in the difference in the half-value width of the transmission peak wavelength between respective wavelengths and thus enables transmission of the transmission peak wavelength with a more uniform half-value width will be described.

Figure 9:
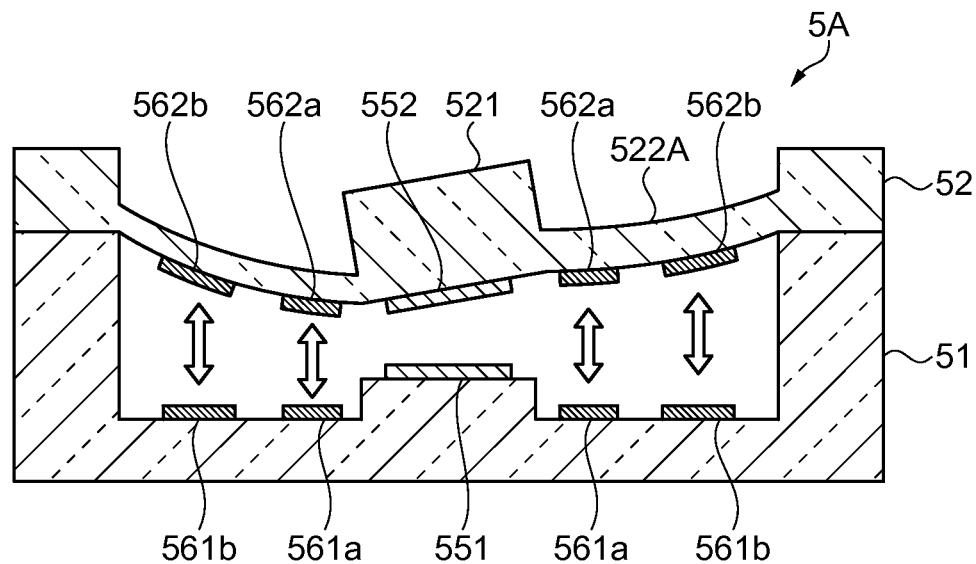
FIG. 9 is a cross-sectional view of a variable-wavelength interference filter according to a second embodiment, in the case where the inter-layer gap is changed.

FIG. 9 is a cross-sectional view of a variable-wavelength interference filter according to the second embodiment, where the inter-layer gap is changed. In FIG. 9, in order to facilitate understanding of the explanation, the gradient angle of the movable portion 521 and the difference in the thickness dimension of a holding portion 522A are exaggerated. Also, in the following description, the same parts of the configuration as in the first embodiment are denoted by the same reference numerals and the explanation thereof is omitted or simplified.

As shown in FIG. 9, in a variable-wavelength interference filter 5A according to the second embodiment, the holding portion 522A on the second substrate 52 is formed in a shape having a thickness dimension that is asymmetrical about the filter center point O. That is, the rigidity of the holding portion 522A in the direction of substrate thickness is asymmetrical about the filter center point O. On the first substrate 51, two concentrically formed first electrodes 561a, 561b are provided. Similarly, on the second substrate 52, two concentrically formed second electrodes 562a, 562b are provided.

In such a holding portion 522A, as shown in FIG. 9, a portion with a large thickness dimension has a high rigidity and does not flex easily when an electrostatic attraction is applied, whereas a portion with a small thickness dimension has a low rigidity and flexes easily when an electrostatic attraction is applied.

Therefore, the gradient of the movable portion 521 (second reflection layer 552) increases as the inter-layer gap G1 increases.

Thus, even in the case where the half-value width of the transmission peak wavelength cannot be made uniform with the configuration of the first embodiment, the half-value width of the transmission peak wavelength can be made uniform in this embodiment.

That is, as the amount of gap of the inter-layer gap G1 decreases, the gradient of the movable portion 521 increases and the half-value width of light of the transmission peak value transmitted through the effective area Ar0 can be increased accordingly. Therefore, the half-value width of the transmission peak wavelength on the short-wavelength side and the half-value width of the transmission peak wavelength on the long-wavelength side can be made uniform.

Third Embodiment

Next, a variable-wavelength interference filter according to a third embodiment of the invention will be described.

In the second embodiment, the thickness dimension of the holding portion 522A is made asymmetrical about the filter center point O, thus causing the movable portion 521 to have a gradient when an electrostatic attraction is applied by the electrostatic actuator 56. Meanwhile, the third embodiment is different from the second embodiment in that the thickness dimension of the holding portion 522 is uniform and that the position where the electrodes constituting the electrostatic actuator 56 are arranged is different.

Figure 10:
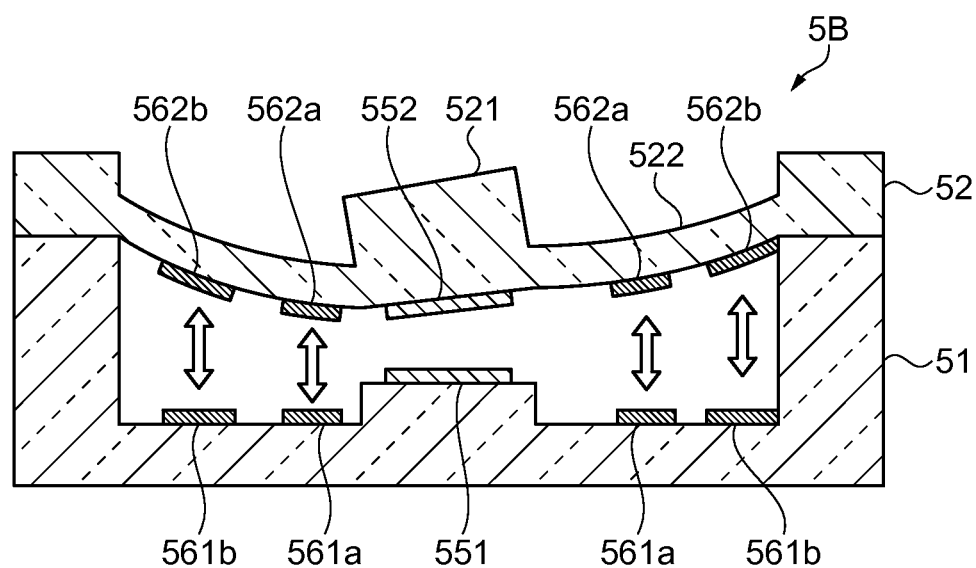
FIG. 10 is a cross-sectional view of a variable-wavelength interference filter according to a third embodiment, in the case where the inter-layer gap is changed.

FIG. 10 is a cross-sectional view of a variable-wavelength interference filter according to the third embodiment, where the inter-layer gap is changed. In FIG. 10, in order to facilitate understanding of the explanation, the gradient angle of the movable portion 521 and the position where the electrostatic actuator 56 is installed are exaggerated.

As shown in FIG. 10, in a variable-wavelength interference filter 5B of the third embodiment, first electrodes 561a, 561b are provided on the first substrate 51, and second electrodes 562a, 562b are provided at positions facing the first electrodes 561a, 561b.

The first electrodes 561a, 561b and the second electrodes 562a, 562b are formed in shapes that are asymmetrical about the filter center point O. Specifically, first electrodes 561a, 561b and the second electrodes 562a, 562b are ring-shaped and the center point of the ring does not coincide with the filter center point O but is eccentric. The first electrodes 561a, 561b may also be provided in a plural number at positions with different distances from the filter center point O, and the second electrodes 562a, 562b may be provided facing the first electrodes 561a, 561b.

In such a configuration, the electrostatic actuator formed by the first electrodes 561a, 561b and the second electrodes 562a, 562b is similarly asymmetrical about the filter center point O. In such a configuration, even when the same electrostatic attraction is applied, the amount of flexure of the holding portion 522 is smaller at the part where the electrostatic actuator is situated on the outer side of the diameter of the holding portion 522, than at the part where the electrostatic actuator is stated on the inner side of the diameter. Therefore, as shown in FIG. 10, when a voltage is applied to the electrostatic actuator, the movable portion 521 (second reflection layer 552) becomes sloped in relation to the first reflection layer 551, and the gradient angle increases as the inter-layer gap G1 increases.

Thus, even in the case where the half-value width of the transmission peak wavelength cannot be made uniform with the configuration of the first embodiment, the half-value width of the transmission peak wavelength can be made uniform in this embodiment.

That is, as the amount of gap of the inter-layer gap G1 decreases, the gradient of the movable portion 521 increases and the half-value width of light of the transmission peak value transmitted through the effective area Ar0 can be increased accordingly. Therefore, the half-value width of the transmission peak wavelength on the short-wavelength side and the half-value width of the transmission peak wavelength on the long-wavelength side can be made uniform.

Also, the holding portion 522A as in the second embodiment may be combined with this embodiment.

In this case, for example, by configuring the first electrodes 561a, 561b and the second electrodes 562a, 562b in such a manner that the electrostatic actuator is situated on the outer side of the diameter at a part where the thickness dimension of the holding portion 522A is large whereas the electrostatic actuator is situated on the inner side of the diameter at apart where the thickness dimension of the holding portion 522A is small, in FIG. 9, the gradient of the movable portion 521 in relation to the inter-layer gap G1 can be increased further.

Also, for example, by configuring the first electrodes 561a, 561b and the second electrodes 562a, 562b in such a manner that the electrostatic actuator is situated on the inner side of the diameter at a part where the thickness dimension of the holding portion 522A is large whereas the electrostatic actuator is situated on the outer side of the diameter at apart where the thickness dimension of the holding portion 522A is small, the gradient state of the movable portion 521 can be finely adjusted.

Fourth Embodiment

Next, a fourth embodiment of the invention will be described.

In the second embodiment and the third embodiment, the configurations in which the gradient angle of the second reflection layer 552 increases as the inter-layer gap G1 decreases are illustrated. Meanwhile, the fourth embodiment is different from the above embodiments in that the amount of flexure of the second reflection layer 552 increases as the inter-layer gap G1 decreases.

Figure 11:
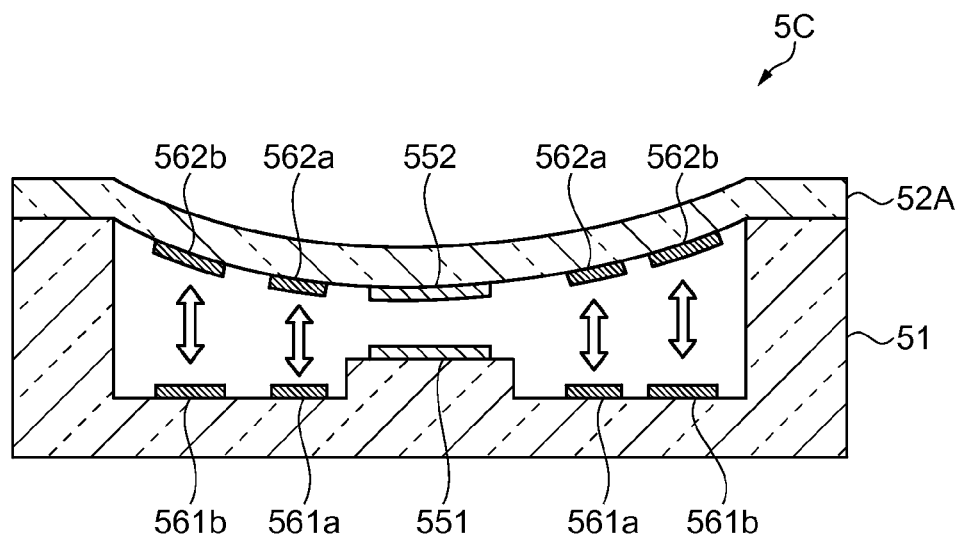
FIG. 11 is a cross-sectional view of a variable-wavelength interference filter according to a fourth embodiment, in the case where the inter-layer gap is changed.

FIG. 11 is a cross-sectional view of a variable-wavelength interference filter according to the fourth embodiment, where the inter-layer gap is changed. In FIG. 11, in order to facilitate understanding of the explanation, the flexure of the second reflection layer 552 is exaggerated.

As shown in FIG. 11, in a variable-wavelength interference filter 5C of the fourth embodiment, a second substrate 52A is formed by a single substrate having a uniform thickness dimension. The thickness dimension of the second substrate 52A is formed, for example, approximately to the dimension of the holding portion 522 of the first embodiment. In this embodiment, the area that is not the bonding portion to be bonded to the first substrate 51, of the second substrate 52A, forms the flexing portion according to the invention.

Therefore, when an electrostatic attraction is applied by the electrostatic actuator, the entire area that is not bonded to the first substrate 51, of the second substrate 52A, flexes toward the first substrate 51 and the inter-layer gap G1 thus changed, as shown in FIG. 11. That is, in this embodiment, as a voltage is applied to the electrostatic actuator, the second reflection layer 552 flexes together with the second substrate 52A and the amount of flexure increases the inter-layer gap G1 decreases.

Therefore, even in the case where the reflectance characteristics of the first reflection layer 551 and the second reflection layer 552 show a greater reflectance on the short-wavelength side than on the long-wavelength side and the half-value width of the transmission peak wavelength through the reflection layers 551, 552 cannot be made uniform with the configuration of the first embodiment, the half-value width of the transmission peak wavelength can be made uniform in this embodiment. That is, the amount of flexure (curvature) of the second reflection layer 552 increases as the gap amount of the inter-layer gap G1 decreases, and the half-value width of light with the transmission peak wavelength transmitted through the effective area Ar0 can be increased accordingly. Therefore, the half-value width of the transmission peak wavelength on the short-wavelength side and the half-value width of the transmission peak wavelength on the long-wavelength side can be made uniform.

Also, since a substrate with a uniform thickness dimension can be used as the second substrate 52A, substrate processing based on etching or the like is not necessary and the manufacturing cost can be reduced.

A substrate that makes the thickness dimension of the second substrate 52A asymmetrical about the filter center point O as in the second embodiment may also be used. Moreover, the position where an electrostatic attraction is applied by the electrostatic actuator 56 may be made asymmetrical about the filter center point O as in the third embodiment.

Fifth Embodiment

Next, a fifth embodiment of the invention will be described with reference to the drawings.

The spectroscopic measuring device 1 of the first embodiment is configured in such a way that the variable-wavelength interference filter 5 is directly provided on the optical module 10. However, there are optical modules having complex configurations and it may be difficult to provide the variable-wavelength interference filter 5 directly thereon, particularly on a small-size optical module. In this embodiment, an optical filter device which enables easy installation of the variable-wavelength interference filter 5 on such an optical module will be described hereinafter.

Figure 12:
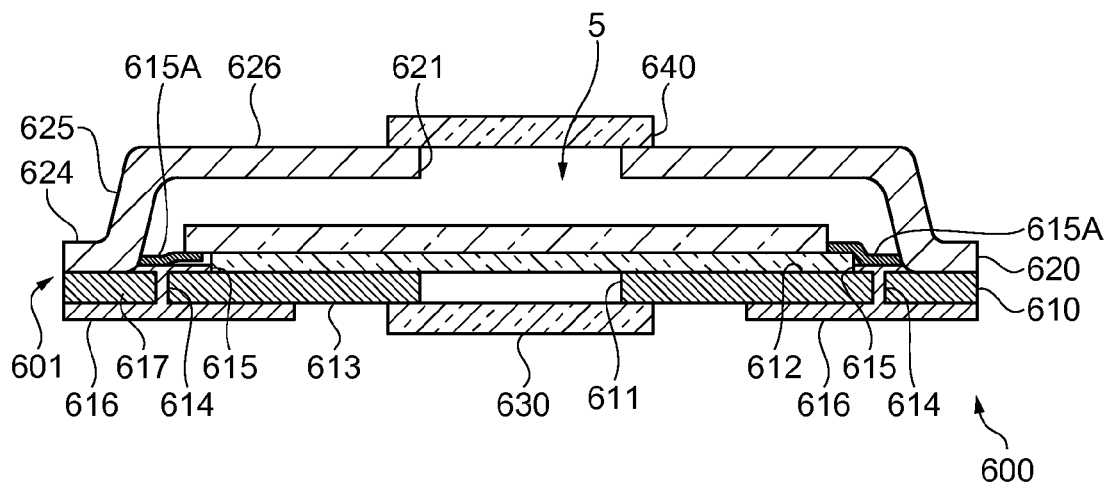
FIG. 12 is a cross-sectional view showing the schematic configuration of an optical filter device according to a fifth embodiment.

FIG. 12 is a cross-sectional view showing the schematic configuration of an optical filter device according to the fifth embodiment of the invention.

As shown in FIG. 12, an optical filter device 600 has a variable-wavelength interference filter 5 and a casing 601 accommodating the variable-wavelength interference filter 5. In this embodiment, the variable-wavelength interference filter 5 is illustrated as an example, but the variable-wavelength interference filters 5A, 5B and 5C of the second to fourth embodiments may also be used.

The casing 601 includes a base substrate 610, a lid 620, a base-side glass substrate 630, and a lid-side glass substrate 640.

The base substrate 610 is made of, for example, a single-layer ceramic substrate. The first substrate 51 of the variable-wavelength interference filter 5 is installed on the base substrate 610. In installing the first substrate 51 on the base substrate 610, for example, the first substrate 51 may be arranged via an adhesive layer or may be fitted with another fixing member or the like. Also, a light transmission hole 611 is opened in an area facing the effective area Ar0, of the base substrate 610. The base-side glass substrate 630 is bonded to cover the light transmission hole 611. As a bonding method for the base-side glass substrate 630, for example, glass frit bonding using glass frit which is glass pieces formed by melting a glass material at a high temperature and then quickly cooling the glass material, or bonding with an epoxy resin or the like can be used.

On a base inner surface 612 facing the lid 620, of the base substrate 610, an inner terminal portion 615 corresponding to each of the lead-out electrodes of the variable-wavelength interference filter 5 is provided. For the connection between each lead-out electrodes 563, 564 and the inner terminal portion 615, for example, an FPC 615A can be used and for example, bonding with an Ag paste, ACF (anisotropic conductive film), ACP (anisotropic conductive paste) or the like can be carried out. This connection is not limited to the connection via the FPC 615A and, for example, wire connection based on wire bonding may be implemented.

Also, on the base substrate 610, a through-hole 614 is formed corresponding to the position where each inner terminal portion 615 is provided. Each inner terminal portion 615 is connected to an outer terminal portion 616 provided on a base outer surface 613 opposite to the base inner surface 612 of the base substrate 610, via an electrically conductive member filling the through-hole 614.

On an outer peripheral part of the base substrate 610, a base bonding portion 617 bonded to the lid 620 is provided.

The lid 620 includes a lid bonding portion 624 bonded to the base bonding portion 617 of the base substrate 610, a sidewall portion 625 continuing from the lid bonding portion 624 and rising in a direction away from the base substrate 610, and a top surface portion 626 continuing from the sidewall portion 625 and covering the first substrate 51 side of the variable-wavelength interference filter 5, as shown in FIG. 12. The lid 620 can be made of, for example, an alloy such as Kovar or a metal.

The lid 620 is tightly bonded to the base substrate 610 as the lid bonding portion 624 and the base bonding portion 617 of the base substrate 610 are bonded together.

The method for this bonding may be, for example, laser welding, soldering with silver solder or the like, sealing with an eutectic alloy layer, welding with low-melting glass, glass adhesion, glass frit bonding, adhesion with an epoxy resin, or the like. Such bonding methods can be properly selected according to the materials of the base substrate 610 and the lid 620 and the bonding environment or the like.

The top surface portion 626 of the lid 620 is parallel to the base substrate 610. In the top surface portion 626, a light transmission hole 621 is opened in an area facing the effective area Ar0 of the variable-wavelength interference filter 5. The lid-side glass substrate 640 is bonded to cover the light transmission hole 621. As a bonding method for the lid-side glass substrate 640, for example, glass frit bonding or adhesion with an epoxy resin or the like can be used, as in the bonding of the base-side glass substrate 630.

Advantageous Effects of Fifth Embodiment

In the optical filter device 600 of this embodiment as described above, since the variable-wavelength interference filter 5 is protected by the casing 601, damage to the variable-wavelength interference filter 5 due to external factors can be prevented.

Other Embodiments

The invention is not limited to the above embodiments and modifications, improvement and the like within a range that can achieve the object of the invention are included in the invention.

With respect to the variable-wavelength interference filters 5, 5A, 5B and 5C, the electrostatic actuator which changes the inter-layer gap G1 to narrow with an electrostatic attraction generated by application of a voltage is illustrated as an example of the gap changing portion. However, the gap changing portion is not limited to this.

For example, instead of each electrode, an electromagnetic actuator in which a coil is arranged may be used to flex the second substrate 52 in a direction to expand the inter-layer gap G1.

Moreover, a piezoelectric actuator may be used instead of the electrostatic actuator 56. In this case, for example, by stacking a lower electrode layer, a piezoelectric film and an upper electrode layer on the holding portion and varying the voltage applied between the lower electrode layer and the upper electrode layer as an input value, the piezoelectric film can be made to expand or contract, thus flexing the holding portion.

Also, while the spectroscopic measuring device 1 is illustrated in the first embodiment as an example of the electronic apparatus according to the invention, the variable-wavelength interference filter, the optical filer device, the optical module and the electronic apparatus of the invention can be used in various fields.

For example, the invention can be used as a light-based system for detecting the existence of a specific substance. As such a system, a gas detecting apparatus such as a gas leakage detector for a vehicle which detects a specific gas with a high sensitivity by employing a spectroscopic measuring method using the variable-wavelength interference filter of the invention or an optoacoustic rare gas detector can be illustrated as an example.

An example of such a gas detecting apparatus will be described hereinafter with reference to the drawings.

Sixth Embodiment

Figure 13:
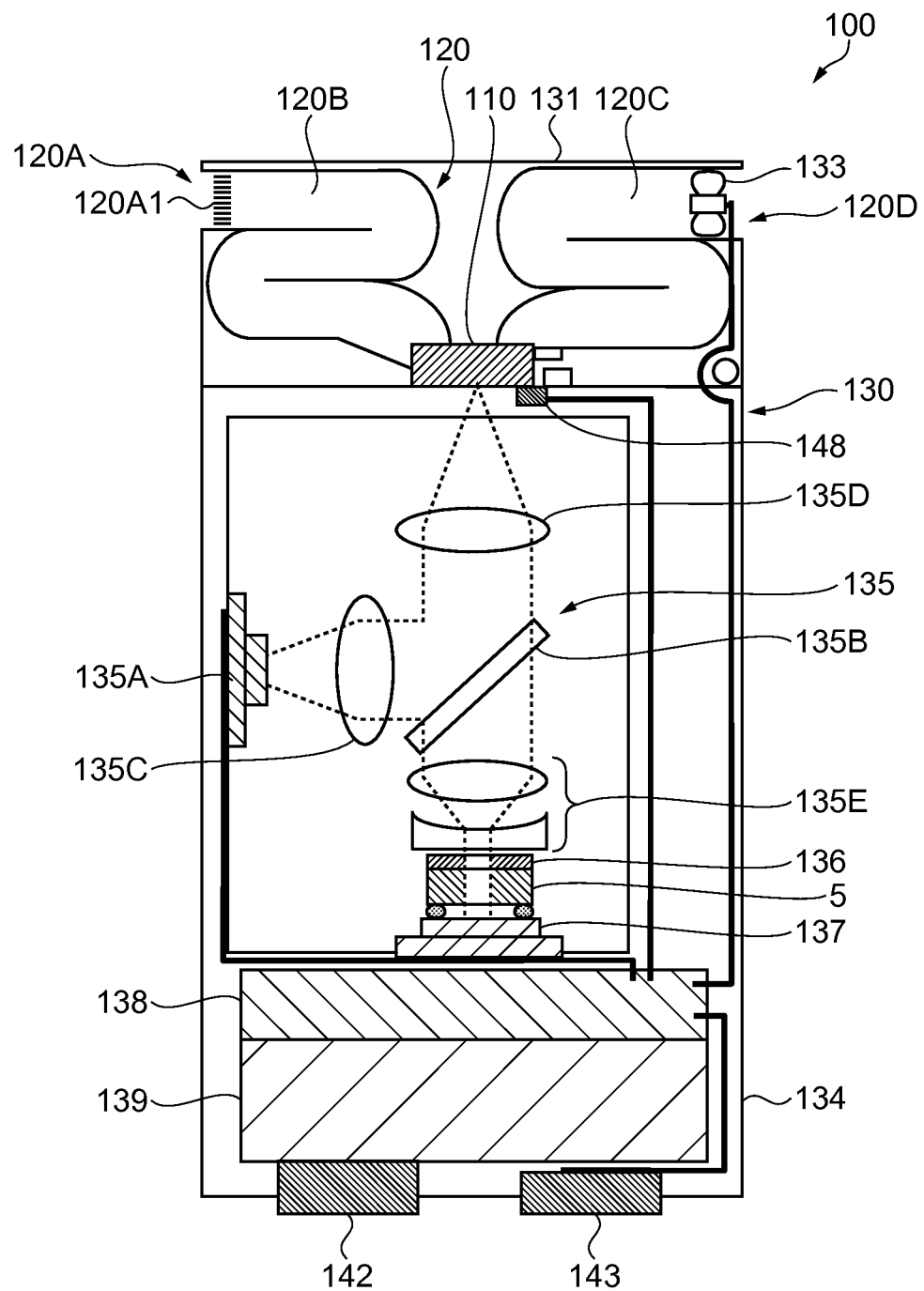
FIG. 13 is a schematic view showing a gas detecting apparatus (electronic apparatus) having a variable-wavelength interference filter according to a sixth embodiment.

FIG. 13 is a schematic view showing an example of a gas detecting apparatus having a variable-wavelength interference filter.

Figure 14:
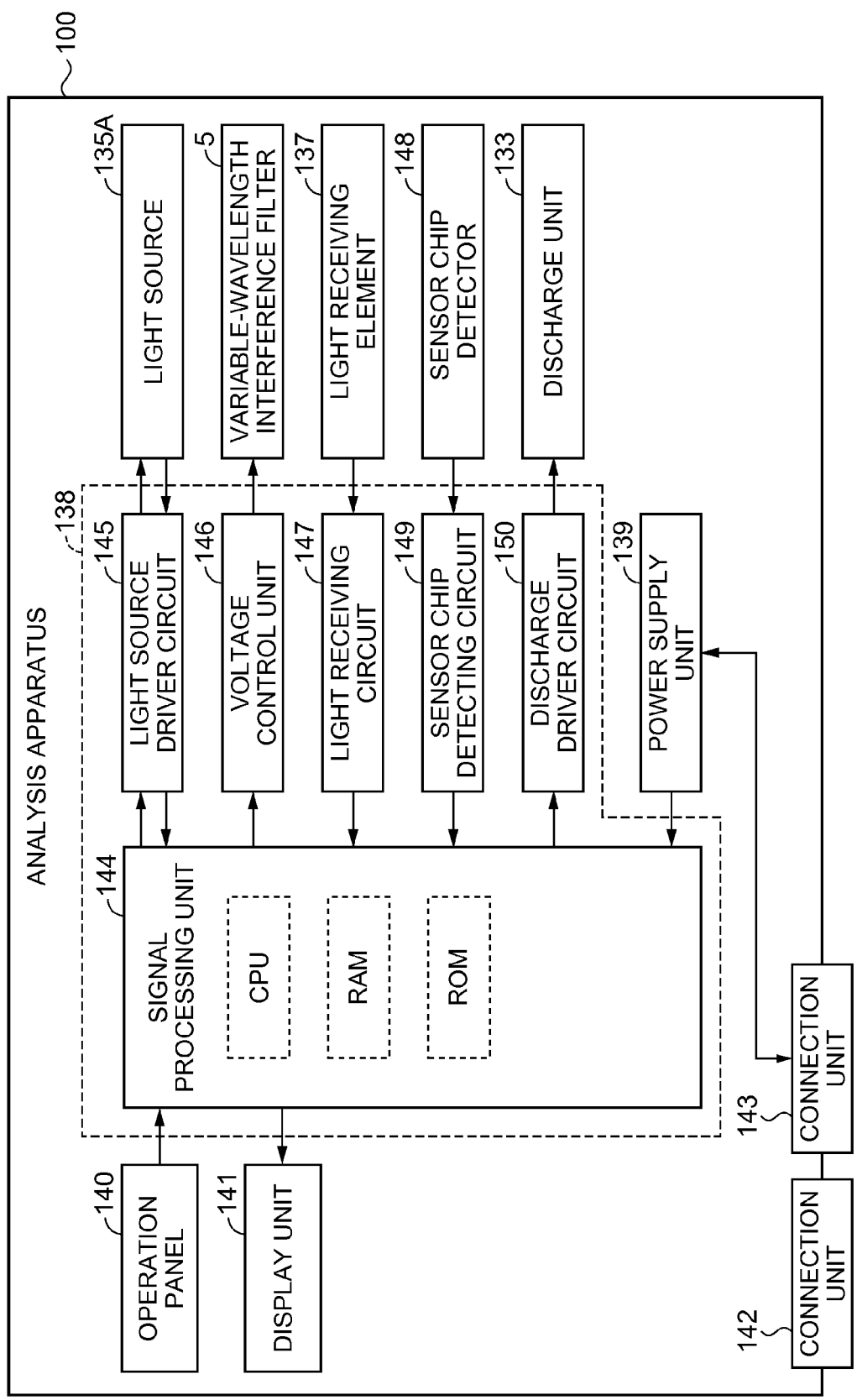
FIG. 14 is a block diagram showing the configuration of a control system of the gas detecting apparatus according to the sixth embodiment.

FIG. 14 is a block diagram showing the configuration of a control system of the gas detecting apparatus of FIG. 13.

This gas detecting apparatus 100 includes: a sensor chip 110; a flow path 120 including a suction port 120A, a suction flow path 120B, discharge flow path 120C, and a discharge port 120D; and a main body unit 130, as shown in FIG. 13.

The main body unit 130 includes: a detecting device including a sensor unit cover 131 having an opening through which the flow path 120 can be attached and removed, a discharge unit 133, a casing 134, an optical unit 135, a filter 136, a variable-wavelength interference filter 5 and a light receiving element 137 (detecting portion) or the like; a control unit 138 which processes a detected signal and controls the detecting portion; a power supply unit 139 which supplies electric power, and the like. Also, the optical unit 135 includes a light source 135A which emits light, a beam splitter 135B which reflects incident light from the light source 135A toward the sensor chip 110 and transmits incident light from the sensor chip side toward the light receiving element 137, and lenses 135C, 135D, 135E. Instead of the variable-wavelength interference filter 5, the variable-wavelength interference filters 5A, 5B, 5C, 5D, 5E or the optical filter device 600 may also be arranged.

As shown in FIG. 14, an operation panel 140, a display unit 141, a connection unit 142 for interfacing with outside, and the power supply unit 139 are provided on a surface of the gas detecting apparatus 100. If the power supply unit 139 is a rechargeable battery, a connection unit 143 for charging may be provided.

Moreover, the control unit 138 of the gas detecting apparatus 100 includes a signal processing unit 144 formed by a CPU or the like, a light source driver circuit 145 for controlling the light source 135A, a voltage control unit 146 for controlling the variable-wavelength interference filter 5, a light receiving circuit 147 which receives a signal from the light receiving element 137, a sensor chip detection circuit 149 which receives a signal from a sensor chip detector 148 that reads a code on the sensor chip 110 and detects whether the sensor chip 110 exists, and a discharge driver circuit 150 which controls the discharge unit 133, and the like, as shown in FIG. 14.

Next, the operation of the above gas detecting apparatus 100 will be described.

The sensor chip detector 148 is provided inside the sensor unit cover 131 at the top of the main body unit 130. The sensor chip detector 148 detects whether the sensor chip 110 exists or not. When the signal processing unit 144 detects a detection signal from the sensor chip detector 148, the signal processing unit 144 determines that the sensor chip 110 is installed, and sends the display unit 141 a display signal to display that detection operation can be implemented.

Then, for example, when the operation panel 140 is operated by a user and an instruction signal to start detection processing is outputted to the signal processing unit 144 from the operation panel 140, the signal processing unit 144 first outputs a signal for light source actuation to the light source driver circuit 145 and thus causes the light source 135A to be actuated. When the light source 135A is driven, a stable laser beam with a single wavelength and linear polarization is emitted from the light source 135A. Also, a temperature sensor and an amount of light sensor are provided inside the light source 135A and information from these sensors is outputted to the signal processing unit 144. When the signal processing unit 144 determines that the light source 135A is stably operating, based on the temperature and the amount of light inputted from the light source 135A, the signal processing unit 144 controls the discharge driver circuit 150 to actuate the discharge unit 133. Thus, a sample gas containing a target substance (gas molecules) to be detected is guided from the suction port 120A to the suction flow path 120B and into the sensor chip 110, then to the discharge flow path 120C and the discharge port 120D. A duct filter 120A1 is provided in the suction port 120A and removes relatively large dust particles and some water vapor or the like.

The sensor chip 110 is a sensor which has plural metal nanostructures incorporated therein and utilizes localized surface plasmon resonance. In such a sensor chip 110, an enforced field is formed between the metal nanostructures by a laser beam, and when gas molecules enter this enhance field, Raman-scattered light and Rayleigh-scattered light containing information of molecular vibration are generated.

Such Rayleigh-scattered light and Raman-scattered light pass through the optical unit 135 and become incident on the filter 136. The Rayleigh-scattered light is separated by the filter 136 and the Raman-scattered light becomes incident on the variable-wavelength interference filter 5. The signal processing unit 144 controls the voltage control unit 146 to adjust the voltage applied to the variable-wavelength interference filter 5, and the variable-wavelength interference filter 5 is made to spectrally separate the Raman-scattered light corresponding to a detection target gas molecule. After that, when the spectrally separate light is received by the light receiving element 137, a light receiving signal corresponding to the amount of light received is output to the signal processing unit 144 via the light receiving circuit 147.

The signal processing unit 144 compares spectrum data of the Raman-scattered light corresponding to the detection target gas molecule, obtained as described above, with data stored in a ROM, thus determines whether the gas molecule in question is the intended gas molecule or not, and specifies the substance. Also, the signal processing unit 144 causes the display unit 141 to display information of the result and outputs the information outward from the connection unit 142.

In FIGS. 13 and 14, the gas detecting apparatus 100 in which Raman-scattered light is spectrally separated by the variable-wavelength interference filter 5 to carry out gas detection based on the spectrally separated Raman-scattered light is illustrated as an example. However, a gas detecting apparatus which detects absorbance unique to a gas and thus specifies the gas type may also be used. In this case, a gas sensor in which a gas is fed to flow inside and which detects the light absorbed by the gas, of incident light, is used as the optical module according to the invention. A gas detecting apparatus in which such a gas sensor analyses and determines the gas flowing inside the sensor is used as the electronic apparatus according to the invention. With such a configuration, a gas component can be similarly detected using the variable-wavelength interference filter.

Also, the system for detecting the existence of a specific substance is not limited to the above gas detection, and a substance component analysis apparatus such as a non-invasive measuring apparatus for saccharide based on near-infrared spectroscopy or a non-invasive measuring apparatus for information about food, living body or minerals can be illustrated as an example.

Hereinafter, a food analysis apparatus will be described as an example of the substance component analysis apparatus.

Seventh Embodiment

Figure 15:
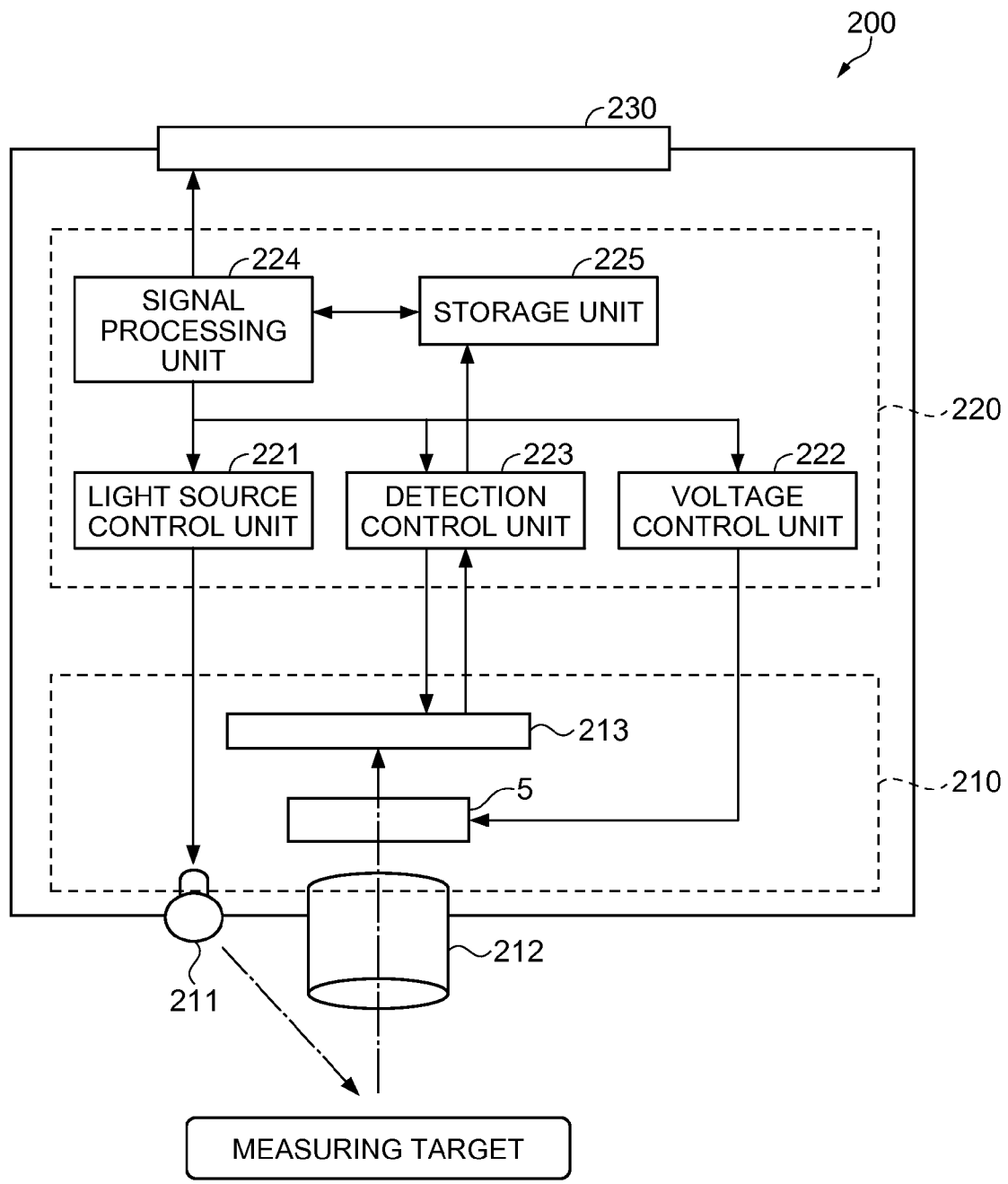
FIG. 15 shows the schematic configuration of a food analysis apparatus (electronic apparatus) having a variable-wavelength interference filter according to a seventh embodiment.

FIG. 15 shows the schematic configuration of a food analysis apparatus as an example of an electronic apparatus utilizing a variable-wavelength interference filter.

This food analysis apparatus 200 includes a detector 210 (optical module), a control unit 220, and a display unit 230, as shown in FIG. 15. The detector 210 has a light source 211 which emits light, an image pickup lens 212 to which light from a measuring target is introduced, the variable-wavelength interference filter 5 which spectrally separates the light introduced from the image pickup lens 212, and an image pickup unit 213 (detecting unit) which detects the spectrally separated light. Instead of the variable-wavelength interference filter 5, the variable-wavelength interference filter 5A, 5B, 5C, 5D, 5E or the optical filter device 600 may be arranged.

The control unit 220 includes a light source control unit 221 which performs on and off-control of the light source 211 and brightness control when the light source is on, a voltage control unit 222 which controls the variable-wavelength interference filter 5, a detection control unit 223 which controls the image pickup unit 213 and acquires a spectral image picked up by the image pickup unit 213, a signal processing unit 224, and a storage unit 225.

In this food analysis apparatus 200, when the system is driven, the light source 211 is controlled by the light source control unit 221 and light is cast onto the measuring target from the light source 211. The light reflected by the measuring target passes through the image pickup lens 212 and becomes incident on the variable-wavelength interference filter 5. Since a voltage that enables spectral separation of a desired wavelength is applied to the variable-wavelength interference filter 5 under the control of the voltage control unit 222, the spectrally separated light is picked up by the image pickup unit 213 made up, for example, of a CCD camera or the like. The picked-up image is stored as a spectral image in the storage unit 225. The signal processing unit 224 controls the voltage control unit 222 to change the voltage value applied to the variable-wavelength interference filter 5, and thus acquires a spectral image with respect to each wavelength.

The signal processing unit 224 performs arithmetic processing of data of each pixel in each image stored in the storage unit 225 and thus finds the spectrum of each pixel. In the storage unit 225, for example, information about components of food with respect to spectrum is stored. The signal processing unit 224 analyzes the calculated spectrum data, based on the information about food stored in the storage unit 225, and thus finds food components contained in the detection target and the content thereof. Also, food calories, freshness and the like can be calculated based on the acquired food components and the content thereof. Moreover, by analyzing the spectral distribution within the image, extraction of a portion where freshness is lowered, in the inspection target food, or the like can be carried out. Also, a foreign matter or the like contained in the food can be detected.

Then, the signal processing unit 224 carries out processing to cause the display unit 230 to display information of the components of the inspection target food, the content, calories and freshness thereof or the like, acquired as described above.

While the food analysis apparatus 200 is illustrated as an example in FIG. 15, a substantially similar configuration can be utilized as a non-invasive measuring apparatus for other types of information as described above. For example, a similar configuration can be used as a bioanalysis apparatus which analyzes biological components, for example, measurement and analysis of components of bodily fluids such as blood. As such a bioanalysis apparatus, an apparatus which detects ethyl alcohol may be used for measuring components of bodily fluids such as blood and thus can be used as a drunk-driving prevention apparatus which detects the driver's drunk state. An electronic endoscope including such a bioanalysis apparatus can also be used.

Moreover, the above configuration can also be used as a mineral analysis apparatus which analyzes components of minerals.

Furthermore, the variable-wavelength interference filter, the optical module and the electronic apparatus according to the invention can be applied to the following apparatuses.

For example, by changing the intensity of light of each wavelength with the passage of time, data can be transmitted on the light of each wavelength. In this case, by spectrally separating light of a specific wavelength with a variable-wavelength interference filter provided in an optical module and causing a light receiving unit to receive the light, data transmitted on the light of the specific wavelength can be extracted. By processing data of light of each wavelength using an electronic apparatus having such a data extraction optical module, optical communication can be implemented.

Eighth Embodiment

As an electronic apparatus, the above configuration can also be applied to a spectroscopic camera, spectroscopic analysis machine or the like which spectrally separates light with the variable-wavelength interference filter according to the invention and thus picks up a spectral image. An example of such a spectroscopic camera may be an infrared camera in which a variable-wavelength interference filter is installed.

Figure 16:
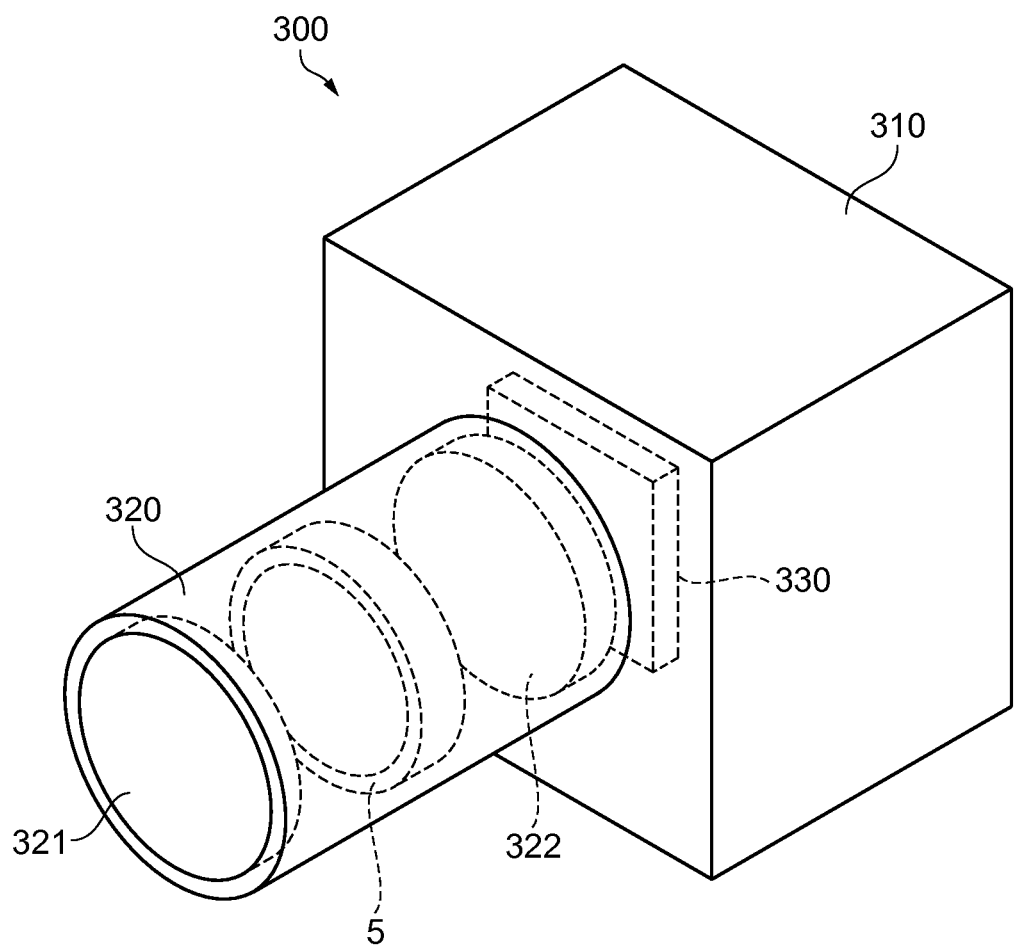
FIG. 16 shows the schematic configuration of a spectroscopic camera (electronic apparatus) having a variable-wavelength interference filter according to an eighth embodiment.

FIG. 16 is a diagram showing the schematic configuration of a spectroscopic camera. A spectroscopic camera 300 includes a camera main body 310, an image pickup lens unit 320, and an image pickup unit 330 (detecting unit), as shown in FIG. 16.

The camera main body 310 is a portion which is held and operated by the user.

The image pickup lens unit 320 is provided on the camera main body 310 and guides incident image light to the image pickup unit 330. Also, the image pickup lens unit 320 includes an objective lens 321, an image forming lens 322, and the variable-wavelength interference filter 5 provided between these lenses, as shown in FIG. 16.

The image pickup unit 330 includes a light receiving element and picks up an image of the image light guided by the image pickup lens unit 320.

In such a spectroscopic camera 300, light of a wavelength to be an image pickup target is transmitted through the variable-wavelength interference filter 5, thus enabling pickup of a spectral image of light of a desired wavelength.

Moreover, the variable-wavelength interference filter according to the invention may be used as a band-pass filter and may be used, for example, for an optical laser apparatus in which only light in a narrow band centering around a predetermined wavelength, of light in a predetermined wavelength range emitted by a light emitting element, is spectrally separated and transmitted by the variable-wavelength interference filter.

Also, the variable-wavelength interference filter according to the invention may be used as a biometric authentication apparatus and can be applied, for example, to an authentication apparatus for blood vessel, fingerprint, retina, iris or the like, using light in a near-infrared range or visible range.

Moreover, the optical module and the electronic apparatus can be used as a concentration detecting apparatus. In this case, infrared energy (infrared rays) emitted from a substance is spectrally separated and analyzed by the variable-wavelength interference filter and the concentration of a test object in a sample is measured.

As described above, the variable-wavelength interference filter, the optical module and the electronic apparatus according to the invention can be applied to any apparatus that spectrally separates predetermined light from incident light. Since the variable-wavelength interference filter according to the invention can spectrally separate plural wavelengths by the single device, as described above, measurement of the spectra of plural wavelengths and detection of plural components can be accurately carried out. Therefore, compared with the related-art apparatus which extracts a desired wavelength using plural devices, miniaturization of the optical module and the electronic apparatus can be accelerated and these devices can be suitably used, for example, as an optical device for mobile use or for vehicle.

In addition, the specific structures for carrying out the invention can be properly changed to other structure within a range that can achieve the object of the invention.

The entire disclosure of Japanese Patent Application No. 2012-114154, filed May 18, 2012 is expressly incorporated by reference herein.

What is claimed is:

1. A variable-wavelength interference filter comprising:
a first substrate;
a second substrate opposed to the first substrate;
a first reflection layer on the first substrate;
a second reflection layer on the second substrate, and opposed to the first reflection layer across a gap; and
a gap changing portion which flexes the second substrate in a direction toward the first substrate and thus changes the gap between the first reflection layer and the second reflection layer;
wherein the first reflection layer and the second reflection layer have a reflectance characteristic showing a higher reflectance to light with a second wavelength that is shorter than a first wavelength, than a reflectance to light with the first wavelength;
the second substrate includes a movable portion provided with the second reflection layer, and a holding portion provided on an outer peripheral part of the movable portion and having a smaller rigidity than the movable portion; and
the rigidity of the holding portion is asymmetrical about a center of movement of the movable portion.

2. The variable-wavelength interference filter according to claim 1,
wherein the first reflection layer and the second reflection layer are made of AlAs.

3. The variable-wavelength interference filter according to claim 1,
wherein the first wavelength is 700 nm and the second wavelength is 400 nm.

4. The variable-wavelength interference filter according to claim 1,
wherein the first wavelength is 2500 nm and the second wavelength is 700 nm.

5. The variable-wavelength interference filter according to claim 1,
wherein the second substrate includes a movable portion provided with the second reflection layer, and a holding portion provided on an outer peripheral part of the movable portion and having a smaller rigidity than the movable portion, and
the gap changing portion is arranged at a position that is asymmetrical about a center of movement of the movable portion in a plan view in which the first substrate and the second substrate are viewed from a direction of substrate thickness.

6. The variable-wavelength interference filter according to claim 1,
wherein the second substrate includes:
a bonding portion bonded to the first substrate; and
a flexing portion which flexes in a direction of approaching from the first substrate with stress applied by the gap changing portion, and
the second reflection layer is provided on the flexing portion.

7. The variable-wavelength interference filter according to claim 6,
wherein the flexing portion has an equal thickness dimension.

8. An optical filter device comprising:
a first substrate;
a second substrate opposed to the first substrate;
a first reflection layer on the first substrate;
a second reflection layer on the second substrate, and opposed to the first reflection layer across a gap;
a gap changing portion which flexes the second substrate in a direction toward the first substrate and thus changes the gap between the first reflection layer and the second reflection layer; and
a casing accommodating the first substrate and the second substrate;
wherein the first reflection layer and the second reflection layer have a reflectance characteristic showing a higher reflectance to light with a second wavelength that is shorter than a first wavelength, than a reflectance to light with the first wavelength;
the second substrate includes a movable portion provided with the second reflection layer, and a holding portion provided on an outer peripheral part of the movable portion and having a smaller rigidity than the movable portion; and
the rigidity of the holding portion is asymmetrical about a center of movement of the movable portion.

9. An optical module comprising:
a first substrate;
a second substrate opposed to the first substrate;
a first reflection layer on the first substrate;
a second reflection layer on the second substrate, and opposed to the first reflection layer across a gap;
a gap changing portion which flexes the second substrate in a direction toward the first substrate and thus changes the gap between the first reflection layer and the second reflection layer; and
a light receiving portion where light transmitted through the first reflection layer or the second reflection layer is received;
wherein the first reflection layer and the second reflection layer have a reflectance characteristic showing a higher reflectance to light with a second wavelength that is shorter than a first wavelength, than a reflectance to light with the first wavelength;
the second substrate includes a movable portion provided with the second reflection layer, and a holding portion provided on an outer peripheral part of the movable portion and having a smaller rigidity than the movable portion; and
the rigidity of the holding portion is asymmetrical about a center of movement of the movable portion.

10. An electronic apparatus comprising:
a first substrate;
a second substrate opposed to the first substrate;
a first reflection layer on the first substrate;
a second reflection layer on the second substrate, and opposed to the first reflection layer across a gap;
a gap changing portion which flexes the second substrate in a direction toward the first substrate and thus changes the gap between the first reflection layer and the second reflection layer;
a light receiving portion where light transmitted through the first reflection layer or the second reflection layer is received; and
an analysis processing portion where, based on the light received by the light receiving portion, a characteristic of the light is analyzed;
wherein the first reflection layer and the second reflection layer have a reflectance characteristic showing a higher reflectance to light with a second wavelength that is shorter than a first wavelength, than a reflectance to light with the first wavelength;

the second substrate includes a movable portion provided with the second reflection layer, and a holding portion provided on an outer peripheral part of the movable portion and having a smaller rigidity than the movable portion; and the rigidity of the holding portion is asymmetrical about a center of movement of the movable portion.

11. A variable-wavelength interference filter comprising:

a first reflection layer; and a second reflection layer arranged opposed to the first reflection layer;

wherein a gap between the first reflection layer and the second reflection layer is changeable, and the first reflection layer and the second reflection layer have a reflectance characteristic showing a higher reflectance to light with a second wavelength that is shorter than a first wavelength, than a reflectance to light with the first wavelength;

wherein at least one of the first reflection layer and the second reflection layer is formed on a substrate including a movable portion and a holding portion that is provided at an outer peripheral part of the movable portion, the holding portion having a smaller rigidity than the movable portion; and the rigidity of the holding portion is asymmetrical about a center of movement of the movable portion.

12. A variable-wavelength interference filter comprising:

a first reflection layer; and a second reflection layer arranged opposed to the first reflection layer;

wherein a gap between the first reflection layer and the second reflection layer is changeable, and the first reflection layer and the second reflection layer have a smaller half-value width of a transmission peak wavelength at a second wavelength that is shorter than a first wavelength, than a half-value width of a transmission peak wavelength at the first wavelength, wherein at least one of the first reflection layer and the second reflection layer is formed on a substrate including a movable portion and a holding portion that is provided at an outer peripheral part of the movable portion, the holding portion having a smaller rigidity than the movable portion; and the rigidity of the holding portion is asymmetrical about a center of movement of the movable portion.

\* \* \* \* \*